(12) United States Patent
Natan et al.

(10) Patent No.: US 8,497,131 B2
(45) Date of Patent: *Jul. 30, 2013

(54) SURFACE ENHANCED SPECTROSCOPY-ACTIVE COMPOSITE NANOPARTICLES COMPRISING RAMAN-ACTIVE REPORTER MOLECULES

(75) Inventors: Michael J. Natan, San Carlos, CA (US); Sharron Gaynor Penn, San Carlos, CA (US); R. Griffith Freeman, Mountain View, CA (US); Gabriela Chakarova, San Jose, CA (US); William E. Doering, Mountain View, CA (US); Ian D. Walton, Redwood City, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1803 days.

This patent is subject to a terminal disclaimer.

(21) Appl. No.: 11/113,601

(22) Filed: Apr. 25, 2005

(65) Prior Publication Data

US 2006/0054506 A1    Mar. 16, 2006

Related U.S. Application Data

(63) Continuation-in-part of application No. 10/345,821, filed on Jan. 16, 2003, now Pat. No. 7,192,778, which is a continuation-in-part of application No. 09/680,782, filed on Oct. 6, 2000, now Pat. No. 6,514,767.

(60) Provisional application No. 60/565,099, filed on Apr. 23, 2004, provisional application No. 60/157,931, filed on Oct. 6, 1999, provisional application No. 60/190,395, filed on Mar. 17, 2000.

(51) Int. Cl.
*G01N 37/00* (2006.01)

(52) U.S. Cl.
USPC ............... 436/56; 436/73; 436/80; 436/166; 436/525; 436/527

(58) Field of Classification Search
None
See application file for complete search history.

(56) References Cited

U.S. PATENT DOCUMENTS

| | | | |
|---|---|---|---|
| 3,975,084 | A | 8/1976 | Block |
| 4,039,297 | A | 8/1977 | Takenaka |
| 4,313,734 | A | 2/1982 | Leuvering |

(Continued)

FOREIGN PATENT DOCUMENTS

| | | |
|---|---|---|
| EP | 0 653 625 | 5/1995 |
| EP | 0 703 454 | 3/1996 |

(Continued)

OTHER PUBLICATIONS

Hoadk et al. "Laser-Induced Inter-Diffusion in AuAg Core-Shell Nanoparticles", J. Phys. Chem. B 2000, v. 104, pp. 11708-11718.*

(Continued)

*Primary Examiner* — Yelena G Gakh
(74) *Attorney, Agent, or Firm* — Mark Lindsey

(57) ABSTRACT

Surface Enhanced Spectroscopy-Active Composite Nanoparticles (SACN) comprising: core/shell nanoparticles comprising nanoparticle cores covered with shells, wherein the cores and the shells may comprise the same or different materials; at least one Raman-active reporter molecule associated with said core/shell nanoparticle; and an $SiO_2$ encapsulant which encapsulates the core/shell nanoparticle and the at least one Raman-active reporter molecule, are described.

15 Claims, 12 Drawing Sheets

U.S. PATENT DOCUMENTS

| | | |
|---|---|---|
| 4,802,761 A | 2/1989 | Bowen et al. |
| 4,853,335 A | 8/1989 | Olsen et al. |
| 4,920,059 A | 4/1990 | Moeremans et al. |
| 5,023,139 A | 6/1991 | Birnboim et al. |
| 5,059,394 A | 10/1991 | Phillips et al. |
| 5,096,809 A | 3/1992 | Chen et al. |
| 5,112,127 A | 5/1992 | Carrabba et al. |
| 5,137,827 A | 8/1992 | Mroczkowski et al. |
| 5,255,067 A | 10/1993 | Carrabba et al. |
| 5,266,498 A | 11/1993 | Tarcha et al. |
| 5,384,265 A | 1/1995 | Kidwell et al. |
| 5,441,894 A | 8/1995 | Coleman et al. |
| 5,445,972 A | 8/1995 | Tarcha et al. |
| 5,552,086 A | 9/1996 | Siiman et al. |
| 5,567,628 A | 10/1996 | Tarcha et al. |
| 5,580,492 A | 12/1996 | Bonnemann et al. |
| 5,609,907 A | 3/1997 | Natan |
| 5,637,508 A | 6/1997 | Kidwell et al. |
| 5,674,699 A | 10/1997 | Saunders et al. |
| 5,825,790 A | 10/1998 | Lawandy |
| 5,828,450 A | 10/1998 | Dou et al. |
| 5,833,924 A | 11/1998 | McClintock et al. |
| 5,864,397 A | 1/1999 | Vo-Dinh |
| 5,891,738 A | 4/1999 | Soini et al. |
| 5,935,755 A | 8/1999 | Kazmaier et al. |
| 5,958,704 A | 9/1999 | Starzl et al. |
| 6,020,207 A | 2/2000 | Liu |
| 6,027,890 A | 2/2000 | Ness et al. |
| 6,103,868 A | 8/2000 | Heath et al. |
| 6,136,610 A | 10/2000 | Polito et al. |
| 6,149,868 A | 11/2000 | Natan et al. |
| 6,200,820 B1 | 3/2001 | Hansen et al. |
| 6,219,137 B1 | 4/2001 | Vo-Dinh |
| 6,235,241 B1 | 5/2001 | Catt et al. |
| 6,274,323 B1 | 8/2001 | Bruchez et al. |
| 6,344,272 B1 | 2/2002 | Oldenburg et al. |
| 6,361,944 B1 | 3/2002 | Mirkin et al. |
| 6,422,998 B1 | 7/2002 | Vo-Dinh et al. |
| 6,436,651 B1 | 8/2002 | Everhart et al. |
| 6,451,619 B1 | 9/2002 | Catt et al. |
| 6,500,622 B2 | 12/2002 | Bruchez, Jr. et al. |
| 6,514,767 B1 | 2/2003 | Natan |
| 6,514,770 B1 | 2/2003 | Sorin |
| 6,558,956 B1 | 5/2003 | Carron et al. |
| 6,562,403 B2 | 5/2003 | Klabunde et al. |
| 6,587,197 B1 | 7/2003 | Rahbar-Dehghan |
| 6,595,427 B1 | 7/2003 | Soni et al. |
| 6,603,537 B1 | 8/2003 | Dietz et al. |
| 6,610,351 B2 | 8/2003 | Shchegolikhin et al. |
| 6,630,307 B2 | 10/2003 | Bruchez et al. |
| 6,642,012 B1 | 11/2003 | Ashdown |
| 6,646,738 B2 | 11/2003 | Roe |
| 6,649,138 B2 | 11/2003 | Adams et al. |
| 6,653,080 B2 | 11/2003 | Bruchez et al. |
| 6,682,596 B2 | 1/2004 | Zehnder et al. |
| 6,687,395 B1 | 2/2004 | Dietz et al. |
| 6,699,724 B1 | 3/2004 | West et al. |
| 6,730,400 B1 | 5/2004 | Komatsu et al. |
| 6,743,581 B1 | 6/2004 | Vo-Dinh |
| 6,750,016 B2 | 6/2004 | Mirkin et al. |
| 6,750,031 B1 | 6/2004 | Ligler et al. |
| 6,759,235 B2 | 7/2004 | Empedocles et al. |
| 6,778,316 B2 | 8/2004 | Halas et al. |
| 6,815,064 B2 | 11/2004 | Treadway et al. |
| 6,815,212 B2 | 11/2004 | Ness et al. |
| 6,838,243 B2 | 1/2005 | Lai et al. |
| 6,861,263 B2 | 3/2005 | Natan |
| 6,919,009 B2 | 7/2005 | Stonas et al. |
| 6,970,246 B2 | 11/2005 | Hansen |
| 6,972,173 B2 | 12/2005 | Su et al. |
| 7,045,049 B1 | 5/2006 | Natan et al. |
| 7,079,241 B2 | 7/2006 | Empedocles et al. |
| 7,098,041 B2 | 8/2006 | Kaylor et al. |
| 7,102,747 B2 | 9/2006 | Wang et al. |
| 7,102,752 B2 | 9/2006 | Kaylor et al. |
| 7,105,310 B1 | 9/2006 | Gray et al. |
| 7,122,384 B2 | 10/2006 | Prober et al. |
| 7,123,359 B2 | 10/2006 | Armstrong et al. |
| 7,141,212 B2 | 11/2006 | Catt et al. |
| 7,192,778 B2 | 3/2007 | Natan |
| 2002/0142480 A1 | 10/2002 | Natan |
| 2003/0232388 A1 | 12/2003 | Kreimer et al. |
| 2005/0036148 A1 | 2/2005 | Phelan |
| 2005/0037510 A1 | 2/2005 | Sharrock et al. |
| 2005/0037511 A1 | 2/2005 | Sharrock |

FOREIGN PATENT DOCUMENTS

| | | |
|---|---|---|
| EP | 1 181 091 | 2/2002 |
| WO | WO 88/07680 | 10/1988 |
| WO | WO 92/17781 | 10/1992 |
| WO | WO 98/04740 | 2/1998 |
| WO | WO 98/10289 | 3/1998 |
| WO | WO 99/21934 | 5/1999 |
| WO | WO 00/11024 | 3/2000 |
| WO | WO 00/27645 | 5/2000 |
| WO | WO 01/08081 | 2/2001 |
| WO | WO 01/25002 | 4/2001 |
| WO | WO 01/25510 | 4/2001 |
| WO | WO 01/25758 | 4/2001 |
| WO | WO 02/29136 | 4/2002 |
| WO | WO 02/68932 | 6/2002 |
| WO | WO 02/079764 | 10/2002 |
| WO | WO 03/021231 | 3/2003 |
| WO | WO 03/021853 | 3/2003 |
| WO | WO 2006/036130 | 4/2006 |
| WO | WO 2006/042111 | 4/2006 |
| WO | WO 2006/105110 | 10/2006 |

OTHER PUBLICATIONS

El-Kouedi et al. (2000) "Optical Properties of Gold-Silver Nanoparticle Pair Structures" J. Phys. Chem., 104:4031-4037.

Sandrock et al. (1999) "Synthesis and Second-Harmonic Generation Studies of Noncentrosymmetric Gold Nanostructures" J. Phys. Chem., 103:2668-2673.

Sandrock et al. (1999) "Synthesis and Linear Optical Properties of Nanoscopic Gold Particle Pair Structures" J. Phys. Chem., 103:11398-11406.

European Patent Office, EP Supplementary Search Report prepared Apr. 18, 2008, for European Patent Application No. EP 05 85 6641, 4 pages.

U.S. Appl. No. 09/598,395, filed Jun. 20, 2000, Nathan & Mallouk.

Akbarian F. et al. Porous Sol-Gel Silicates Containing Gold Particles as Matrices for Surface-Enhanced Raman Spectroscopy; Journal of Raman Spectroscopy; vol. 27, Issue 10, Date: Oct. 1996, pp. 775-783.

Ascencio, Jorge A., et al.; A truncated icosahedral structure observed in gold nanoparticles; Jorge A. Ascencio, Mario Surface Science, vol. 447, Issues 1-3, Feb. 20, 2000, pp. 73-80.

Averitt, Richard D, et al.; A metal nanoshell consists of a nanometer-scale dielectric core surrounded by a thin metallic shell. The plasmon resonance of metal nanoshells displays a geometric tunability, Josa B, vol. 16 Issue 10, pp. 1824-1832 (1999).

Brazdil, James F., et al.; Resonance Raman spectra of adsorbed species at solid-gas interfaces. Nitrosodimethylaniline adsorbed on silica and alumina surfaces J. Phys. Chem., 1981, 85 (8), pp. 995-1004.

Bruchez M Jr., et al.; Semiconductor nanocrystals as fluorescent biological labels; ;Science. Sep. 25, 1998;281(5385):2013-6.

Byahut, S., et al.; Direct comparison of the chemical properties of single crystal Ag(111) and electrochemically roughened Ag as substrates for surface Raman scattering;Langmuir, 1991, 7 (3), pp. 508-513.

Chan WC, et al.; Quantum dot bioconjugates for ultrasensitive nonisotopic detection. Science 281: 2016-18 (1998).

Dhere, A.G., et al.; Twinned colloidal gold particles; Ultramicroscopy, vol. 18, Issues 1-4, 1985, pp. 415-417 (1985).

Duff, D. G., et al.; The Morphology and Microstructure of Colloidal Silver and Gold Angewandte Chemie International Edition in English; vol. 26, Issue 7 , pp. 676-678 (1987).

Emory, Steven R., et al.; Near-Field Surface-Enhanced Raman Spectroscopy on Single Silver Nanoparticles; Anal. Chem., 1997, 69 (14), pp. 2631-2635.

Emory, Steven R., et al.; Screening and Enrichment of Metal Nanoparticles with Novel Optical Properties; J. Phys. Chem. B, 1998, 102 (3), pp. 493-497.

Emory, Steven R., et al.; Direct Observation of Size-Dependent Optical Enhancement in Single Metal Nanoparticles; Journal of the American Chemical Society 1998 120 (31), 8009-8010.

Félidj, Nordin, et al.; A new approach to determine nanoparticle shape and size distributions of SERS-active gold-silver mixed colloids; New J. Chem., 1998, 22, 725-732.

Freeman, R.G., et al.; Ag-Clad Au Nanoparticles: Novel Aggregation, Optical, and Surface-Enhanced Raman Scattering Properties; , M.J; J. Phys. Chem; V.100, n.2, pp. 718-724 (1996).

Grabar, Katherine C., et al. Preparation and Characterization of Au Colloid Monolayers; Anal. Chem., 1995, 67 (4), pp. 735-743.

Hall, Simon R., et al.; Cocondensation of Organosilica Hybrid Shells on Nanoparticle Templates: A Direct Synthetic Route to Functionalized Core-Shell Colloids; Langmuir, 2000, 16 (3), pp. 1454-1456.

Horkans, Jean, et al.; Pulsed Potentiostatic Deposition of Gold from Solutions of the Au(I) Sulfite Complex Electrochem. Soc. 124 1499 (1977).

Jin, Rongchao, et al.; Photoinduced Conversion of Silver Nanospheres to Nanoprisms Science Nov. 30, 2001 294: 1901-1903.

Kneipp, K.; High-sensitive SERS on colloidal silver particles in aqueous solution Journal: Experimentelle Technik der Physik; vol. 36, No. 2, p. 161-6 (1998).

Kneipp, Katrin, et al.; Approach to Single Molecule Detection Using Surface-Enhanced Resonance Raman Scattering (SERRS): A Study Using Rhodamine 6G on Colloidal Silver; Applied Spectroscopy, vol. 49, Issue 6, pp. 12A-20A and 691-860 (Jun. 1995) , pp. 780-784(5).

Kneipp, Katrin, et al.; Population Pumping of Excited Vibrational States by Spontaneous Surface-Enhanced Raman Scattering; ; Phys. Rev. Lett. 76, 2444-2447 (1996).

Kneipp, Katrin, et al.; Single Molecule Detection Using Surface-Enhanced Raman Scattering (SERS); Phys. Rev. Lett. 78, 1667-1670 (1997).

Kneipp, Katrin; et al.; Single-Molecule Detection of a Cyanine Dye in Silver Colloidal Solution Using Near-Infrared Surface-Enhanced Raman Scattering; Applied Spectroscopy, vol. 52, Issue 2, pp. 72A-73A and 175-321 (Feb. 1998) , pp. 175-178(4).

Kneipp, Katrin; et al.; Extremely Large Enhancement Factors in Surface-Enhanced Raman Scattering for Molecules on Colloidal Gold Clusters; Applied Spectroscopy, vol. 52, Issue 12, pp. 443A-455A and 1493-1626 (Dec. 1998) , pp. 1493-1497(5).

Kneipp, Katrin, et al.: Detection and identification of a single DNA base molecule using surface-enhanced Raman scattering (SERS); Rev. E 57, R6281-R6284 (1998).

Kneipp, Katrin, et al.; Ultrasensitive Chemical Analysis by Raman Spectroscopy; Chem. Rev., 1999, 99 (10), pp. 2957-2976.

Kneipp, Katrin, et al.; Surface-enhanced Raman scattering: A new tool for biomedical spectroscopy; Current Science, vol. 77 No. 7, p. 915-926 Oct. 10, 1999.

Kovtyukhova, Nina I., et al.; Layer-by-Layer Assembly of Rectifying Junctions in and on Metal Nanowires; J. Phys. Chem. B, 2001, 105 (37), pp. 8762-8769.

Liz-Marzán, Luis M., et al.; Synthesis of Nanosized Gold-Silica Core-Shell Particles;; Langmuir, 1996, 12 (18), pp. 4329-4335.

Lyon William A., et al.; Confinement and Detection of Single Molecules in Submicrometer Channels; Anal. Chem., 1997, 69 (16), pp. 3400-3405.

Michaels, Amy M., et al. Junctions as the Site for Surface-Enhanced Raman Scattering of Single Rhodamine 6G Molecules; ;J. Phys. Chem. B, 2000, 104 (50), pp. 11965-11971.

Michaels, Amy M., et al.: Surface Enhanced Raman Spectroscopy of Individual Rhodamine 6G Molecules on Large Ag Nanocrystals; ; J. Am. Chem. Soc., 1999, 121 (43), pp. 9932-9939.

Mucic, Robert C., et al; DNA-Directed Synthesis of Binary Nanoparticle Network Materials; J. Am. Chem. Soc., 1998, 120 (48), pp. 12674-12675.

Ni, Jing, et al.; Immunoassay Readout Method Using Extrinsic Raman Labels Adsorbed on Immunogold Colloids; ; Anal. Chem., 1999, 71 (21), pp. 4903-4908.

Nicewarner SR, et al.; Synthesis and characterization of well-defined metal nanoparticle-protein-metal nanoparticle sandwiches; Penn State Univ./University Pk//Pa/16802; Abstracts of Papers of The American Chemical Society , 1998 , V 216 , 1 ( Aug. 23) , p. 172-COLL.

Nicewarner-Peña, Sheila R., et al.; Metallic Barcodes; Science Oct. 5, 2001; 294: 137-141.

Nie, Shuming, et al.; Single Molecules and Single Nanoparticles by Surface-Enhanced Raman Scattering; Emory; Science Feb. 21, 1997:vol. 275. No. 5303, pp. 1102-1106.

Nie, Shuming; Optical detection of single molecules; Annual Review of Biophysics and Biomolecular Structure vol. 26: 567-596 (1997).

Nikoobakht, Babak, et al.; Preparation and Growth Mechanism of Gold Nanorods (NRs) Using Seed-Mediated Growth Method; Chem. Mater. 2003, 15, 1957-1962.

Ron, Hannoch, et al.; Self-Assembled Monolayers on Oxidized Metals. 2. Gold Surface Oxidative Pretreatment, Monolayer Properties, and Depression Formation; ; Langmuir, 1998, 14 (5), pp. 1116-1121.

Shibata, S., et al.; Preparation of Silica Microspheres Containing Ag Nanoparticles; Journal of Sol-Gel Science and Technology vol. 11, No. 3 / Aug. 1998.

Stöber, Werner, et al.; Controlled growth of monodisperse silica spheres in the micron size range; Journal of Colloid and Interface Science, vol. 26, Issue 1, Jan. 1968, pp. 62-69.

Sun, L., et al.; Fabrication of nanoporous single crystal mica templates for electrochemical deposition of nanowire arrays; Journal of Materials Science, vol. 35, No. 5 / Mar. 2000, pp. 1097-1103.

Switzer Jay A., et al.; Electrochemical Self-Assembly of Copper/Cuprous Oxide Layered NanostructuresJ. Am. Chem. Soc., 1998, 120 (14), pp. 3530-3531.

Ung, Thearith, et al.; Controlled Method for Silica Coating of Silver Colloids. Influence of Coating on the Rate of Chemical Reactions Langmuir, 1998, 14 (14), pp. 3740-3748.

Van Duyne, R., et al.; Atomic force microscopy and surface-enhanced Raman spectroscopy. I. Ag island films and Ag film over polymer nanosphere surfaces supported on glass Chem. Phys. / vol. 99 / Issue 3 / p. 2101-2115.

Vo-Dinh Tuan; Surface-enhanced Raman Spectroscopy using metallic nanostructures Trends in Analytical Chemistry, vol. 17, No. 8-9, 1998, XP002314222.

Walton, Ian D., et al.; Particles for Multiplexed Analysis in Solution: Detection and Identification of Striped Metallic Particles Using Optical Microscopy Anal. Chem., 2002, 74 (10), pp. 2240-2247.

Co-Pending U.S. Appl. No. 11/051,222, filed Feb. 4, 2005.
Co-Pending U.S. Appl. No. 11/132,510, filed May 18, 2005.
Co-Pending U.S. Appl. No. 11/132,974, filed May 18, 2005.
Co-Pending U.S. Appl. No. 11/133,926, filed May 20, 2005.
Co-Pending U.S. Appl. No. 11/134,129, filed May 20, 2005.
Co-Pending U.S. Appl. No. 11/134,145, filed May 20, 2005.
Co-Pending U.S. Appl. No. 11/611,052, filed Dec. 14, 2006.
Co-Pending U.S. Appl. No. 11/622,915, filed Jan. 12, 2007.
Co-Pending U.S. Appl. No. 12/245,538, filed Oct. 3, 2008.
Co-Pending U.S. Appl. No. 12/245,555, filed Oct. 3, 2008.
U.S. Appl. No. 09/676,890, filed Oct. 2, 2000, Natan et al.
U.S. Appl. No. 09/677,198, filed Oct. 2, 2000, Nathan et al.

Akerman et al., "Nanocrystal targeting in vivo" PNAS, 99 (20), 2002, p. 12617-12621.

Ballou et al., "Nonivasive imaging of quantum dots in mice", Bioconjugate Chem., 15 (1), 2004, pp. 79-86.

Gao et al., "In vivo cancer targeting and imaging with semiconductor quantum dots", Nature Biotechnology, 22 (8), 2004, pp. 969-976.

Hua-Zhong Yu et al., "Surface-Enhanced Raman Scattering (SERS) from Azobenzene Self-Assembled Sandwiches", Langmuir, vol. 15, No. 1, 1999, pp. 16-19.

Keating et al., "Heightened Electromagnetic Fields Between Metal Nanoparticles: Surface Enhanced Raman Scattering from Metal-Cytochrome c-Metal Sandwiches", J. Phys. Chem. B, vol. 102, No. 47, 1998, pp. 9414-9425.

Keating et al., "Protein: Colloid Conjugates for Surface Enhanced Raman Scattering: Stability and Control of Protein Orientation", J. Phys. Chem. B, vol. 102, No. 47, 1998, pp. 9404-9413.

Moskovits et al., "SERS and the Single Molecule: Near Field Microscopy and Spectroscopy", SPIE, 2001, vol. 4258, pp. 43-49.

Wasileski et al., "Surface-Enhanced Raman Scattering from Substrates with Conducting or Insulator Overlayers: Electromagnetic Model Predictions and Comparisons with Experiment", Applied Spectroscopy, 2000, vol. 54, pp. 761-772.

\* cited by examiner

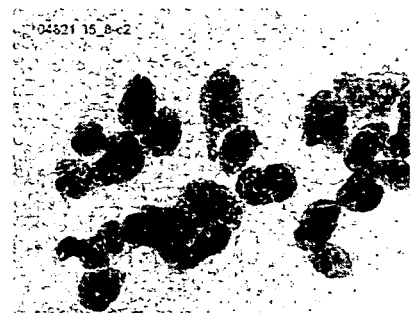
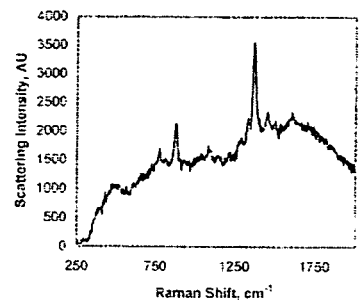
Figure 14A                    Figure 14B
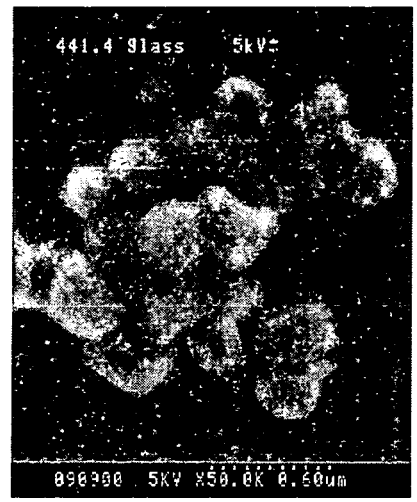
Figure 15A                    Figure 15B
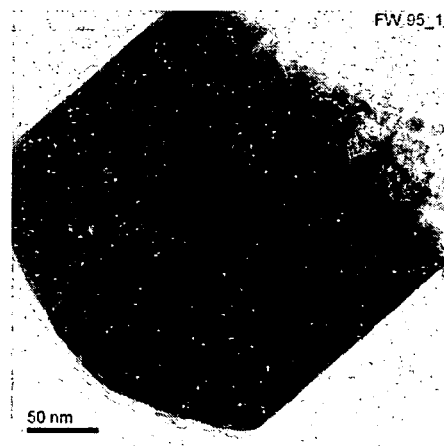
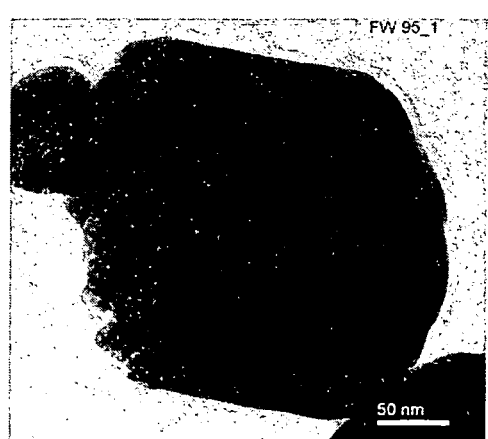
Figure 16A                    Figure 16B

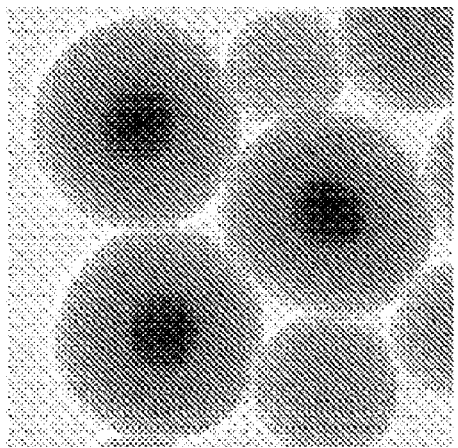 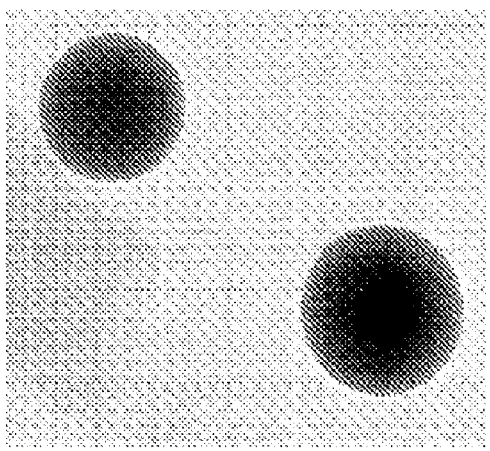
Figure 24A                    Figure 24B
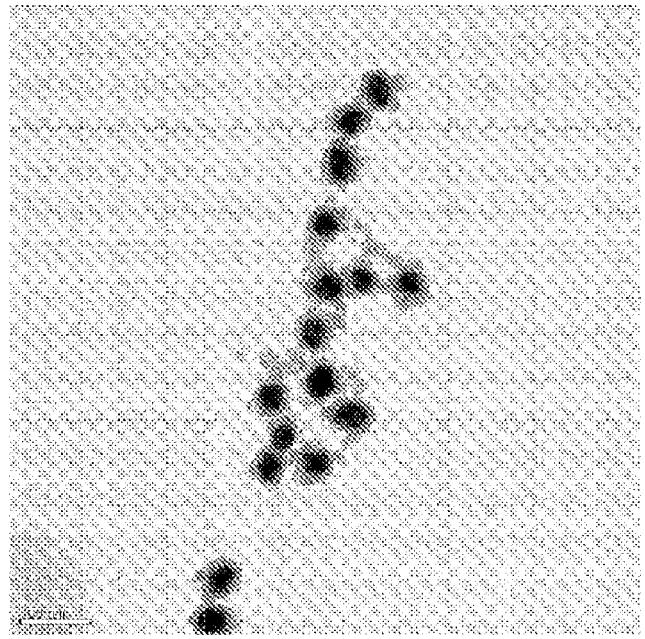
Figure 25

SURFACE ENHANCED SPECTROSCOPY-ACTIVE COMPOSITE NANOPARTICLES COMPRISING RAMAN-ACTIVE REPORTER MOLECULES

CROSS-REFERENCE TO RELATED APPLICATIONS

This application claims the benefit under 35 U.S.C. §119, of U.S. Provisional Patent Application Ser. No. 60/565,099, entitled "Surface Enhanced Spectroscopy-Active Composite Nanoparticles," filed Apr. 23, 2004. This application is a continuation-in-part of U.S. patent application Ser. No. 10/345,821, entitled, "Surface Enhanced Spectroscopy-Active Composite Nanoparticles," filed Jan. 16, 2003 now U.S. Pat. No. 7,192,778, which is a continuation-in-part of U.S. patent application Ser. No. 09/680,782, entitled "Surface Enhanced Spectroscopy-Active Composite Nanoparticles", filed Oct. 6, 2000, and now U.S. Pat. No. 6,514,767, which claims the benefit under 35 U.S.C. §119, of U.S. Provisional Patent Application Ser. No. 60/157,931, entitled, "Glass Coated Surface Enhanced Raman Scattering Tags," filed Oct. 6, 1999, and U.S. Provisional Patent Application Ser. No. 60/190,395, entitled "GANS Particles," filed Mar. 17, 2000. Each of the foregoing applications is incorporated by reference herein in its entirety.

GOVERNMENT LICENSE RIGHTS

The U.S. Government has a paid-up license in this invention and the right in limited circumstances to require the patent owner to license others on reasonable terms as provided for by the terms of Grant No. 1R43CA111752-01 awarded by NIH/NCI, and Grant No. 70NAB1H3028 awarded by NIST.

FIELD OF THE INVENTION

This invention relates generally to submicron-sized particles or labels that can be covalently or non-covalently affixed to entities of interest for the purpose of quantification, location, identification, or tracking. More particularly, it relates to surface enhanced spectroscopy-active composite nanoparticles, methods of manufacture of the particles, and uses of the particles.

BACKGROUND OF THE INVENTION

Fluorescence is a primary means by which biomolecules are tracked and quantitated. Fluorescent tags are used in DNA sequencing, gene expression analysis using microarrays, flow cytometry and its variants, RT-PCR, and a host of other applications. One application of special interest, and increasing importance, is intracellular imaging. Bimolecular binding/debinding events have been monitored by fluorescence resonance energy transfer (FRET), whereby event-driven changes in the distance between a fluorophore and quencher lead to changes in fluorescence intensity. Covalent attachment of fluorophores to surface antibody markers on white blood cells is the basis of cytometry; likewise covalent attachment of fluorescent tags has been used to visualize every organelle within a cell, and virtually every process that cells undergo. Despite their numerous strengths, organic fluorophores have several limitations. (i) They are highly susceptible to photobleaching and photodecomposition as excited states are both better oxidants and better reductants than the ground state. (ii) The fluorescence emission envelope is broad, limiting the number of spectrally orthogonal tags. (iii) The fluorescence is typically excited in the visible, a region where biological samples exhibit intrinsic background fluorescence. (iv) different colors of fluorophores often have vastly different structures and chemical properties, necessitating different attachment and handling protocols.

The development of fluorescent nanoparticulate semiconductors (quantum dots) has extended the utility of fluorescence-based optical detection tags. (Chan, et al., Science 1998, 281, 2016-18; Bruchez, et al., Science 1998, 281, 2013-16.) The disclosure of Chan, et al., and all other patents, patent applications, and publications referred to herein are incorporated by reference herein in their entirety. Quantum dots exhibit far less photobleaching than organic fluorophores, and in the visible, have narrower emission bandwidths. A consequence of the narrower emission envelope, though, is the narrower excitation envelope in the visible; as a result, ultraviolet light is required to excite multiple tags, which is less than optimal for biological systems. Moreover, bandwidths of quantum dots increase considerably as the particles emit in the red and especially in the near-IR, and accordingly, many fewer colors are available. Nevertheless, quantum dots have been used extensively for intracellular imaging applications, with promising results. Recent reports have used quantum dots to track the binding and endocytosis of epidermal-growth factor and for long-term imaging of quantum dots that were endocytosed or attached to biotinylated surface proteins of living cells. However, the bulk of the literature describes non-targeted approaches to cellular delivery. A peptide translocation domain was used to introduce various ratios of 5 colors of quantum dots into cell subsets to produce 10 unique codes. Various reports describe tracking of cells injected into mice after being encoded by quantum dots, including using a lipofection reagent and transduction peptides. Development of Xenopus embryos was also tracked after injection of micelle-encapsulated quantum dots. Unfortunately, endocytosed quantum dots are sequestered and not able to participate in further intracellular labeling and quantum dots delivered by transfection and electroporation are prone to aggregation. Microinjection allows delivery of unaggregated quantum dots, but is a serial process requiring much skill. Additionally, the long-term imaging with UV light can cause degradation of the quantum dots, resulting in spectral shifts and cytotoxicity. Likewise, the introduction of metal nanoparticles into cells has been described. Metal nanoparticles were shown to be successfully introduced inside living cells in 1990, when electron microscopy was used to examine nuclear uptake of colloidal gold microinjected into the cytoplasm. (Feldherr, et al, J Cell Biol 1990, 111, 1-8; Feldherr, et al., J Cell Biol 1991, 115, 933-39.) The art was advanced by using video-enhanced color microscopy to track the nuclear targeting ability of peptide modified colloidal gold. Several reports have taken advantage of the strong plasmon resonance from Ag and Au nanoparticles by modifying them with biological molecules to track the dynamics of membrane-transporter protein on living cells in real time. The absence of photobleaching in both techniques allows long-term imaging without any degradation of the particles. In theory, particle size, shape and composition may be controlled to allow multiplexed plasmon resonance imaging experiments, but in practice, the width of features coupled with difficulty in making all particles a given size reduce the number of colors to 2-3.

Raman scattering is readily excited using monochromatic far-red or near-IR light, photon energies too low to excite the inherent background fluorescence in biological samples. Since Raman spectra typically cover vibrational energies from 200-3500 $cm^{-1}$, and since individual vibrations typically have very narrow bandwidths, i.e. <50 cm$^{-1}$, one could envisage measuring a dozen (or more) reporters simultaneously, all with a single light source; however, normal Raman is very weak, limiting its utility for use in bioanalytical chemistry. In SERS, molecules in very close proximity to nanoscale roughness features on noble metal surfaces (gold, silver, copper) give rise to million- to trillion-fold increases [known as enhancement factor (EF)] in scattering efficiency. SERS can also be used to detect molecules adsorbed to individual metal nanoparticles and has been used to demonstrate the detection of a single molecule.

SUMMARY OF THE INVENTION

The present invention provides a method, comprising: causing deposition of a metal into a pore of a template, the pore diameter of which is less than 300 nm; causing deposition of a second material into said pore of said template, wherein the deposition of at least one of said first material and said second material involves faradaic electrochemical processes to generate a segmented, pore-bound nanoparticle; repeating the deposition of a metal; and releasing said second material and said template from said segmented, pore-bound nanoparticle to generate at least two free metal nanoparticles. The present invention also provides a method, comprising causing deposition of a first metal into a pore of a template, the pore diameter of which is less than 300 nm; causing deposition of a second metal into said pore of said template; causing deposition of a third material into said pore of said template, wherein the deposition of at least one of said first material and said second material involves faradaic electrochemical processes to generate a segmented, pore-bound nanoparticle; repeating the steps of depositing a first metal and a second metal; and releasing said third material and said template from said segmented, pore-bound nanoparticle to generate a at least two free metal nanoparticles, each comprising said first metal and said second metal.

The present invention also provides a method, comprising, preparing an optimized SACN, wherein said optimized SACN is prepared by a method comprising removing material irreversibly bound to the particle surface during the course of preparing the SACN, wherein background signal of said spectrum is reduced compared to a spectrum generated by a corresponding SACN which is not optimized.

The present invention also provides a method, comprising reducing the background signal in an assay utilizing a SACN particle, wherein said reducing comprises removing impurities from a component selected from the group consisting of the sample to be analyzed, the SACN particle, and the assay vessel.

The present invention also provides a method, comprising preparing a plurality of SACN particles, each comprising a different Raman tag; measuring the intensity ratio of the Raman tags; and preparing a second plurality of SACN particles having the intensities of the tags normalized to that of the tag that has the weakest intensity, whereby a plurality of SACNs having substantially equal peak intensities in a Raman spectrum are prepared. In some embodiments, the tags are normalized by preparing SACNs with a decreased quantity of tag, wherein the decreased quantity is defined by the inverse of the intensity ratio of that tag to that of the weakest tag. In other embodiments, the tags are normalized by preparing SACNs with an increased quantity of silane, wherein the increased quantity is defined by the inverse of the intensity ratio of that tag to that of the weakest tag.

The present invention also provides a SACN, comprising a nanoparticle core, a Raman-active reporter molecule, an SiO$_2$ encapsulant, and a reactive group selected from the group consisting of an —SH group, a —NH$_2$ group, and a —COO$^-$ group. The present invention also provides a method, comprising: providing a nanoparticle; associating a Raman-active reporter molecule with said nanoparticle; encapsulating the nanoparticle with SiO$_2$; and modifying the SiO$_2$ to bear a reactive group selected from the group consisting of an —SH group, a —NH$_2$ group, and a —COO$^-$ group, whereby an activated SACN is prepared.

The present invention also provides a bioconjuated SACN, comprising: a nanoparticle; a Raman-active reporter molecule associated with said nanoparticle; an SiO$_2$ encapsulant; and a biomolecule selected from the group consisting of a protein and a nucleic acid.

The present invention also provides a method for detecting an analyte comprising: obtaining a biological sample; and contacting the sample with a bioconjugated SACN comprising a biomolecule that binds to the analyte: and detecting the analyte bound to said bioconjugated SACN.

The present invention also provides a method, comprising; contacting a sample suspected of containing an analyte with at least one specific binding partner to the analyte on a lateral-flow assay surface to bind to the analyte in the sample; previously, simultaneously or subsequently to step (a), binding at least one analyte binding partner with a SACN; and detecting a SERS signal whereby the presence of the analyte is determined in the sample by the intensity or presence of the signal, whereby the presence of at least one analyte in the sample is determined.

The present invention also provides a method, comprising, providing a microscope coupled to a CCD camera; providing a cell; contacting the cell with at least one SACN capable of specifically binding to the cell or a portion of the cell; providing a wavenumber filtering device between the cell and the camera; acquiring a plurality of data sets: and assembling the data sets; whereby a spatial profile of the SACN is acquired.

The present invention also provides a nanoparticle, a metal nanoparticle: more than one Raman-active reporter molecule associated with said nanoparticle; and an SiO$_2$ encapsulant. The present invention also provides a method, comprising: contacting HAuCl$_4$ with hydroxylamine hydrochloride; further contacting the solution resulting from step a) with a mixture of sodium citrate dehydrate and NaBH$_4$, whereby a gold nanoparticle is produced. The present invention also provides a method comprising, providing a gold nanoparticle prepared by the previously described method; associating a Raman-active reporter molecule with said nanoparticle; and encapsulating the nanoparticle with SiO$_2$; whereby a SACN is prepared. The present invention also provides a nanoparticle comprising: a anisotropic metal nanoparticle; a SERS-active reporter molecule associated with said anisotropic metal nanoparticle; SiO$_2$ encapsulating the anisotropic metal nanoparticle.

The present invention also provides a method comprising; administering a SACN nanoparticle imaging agent to a patient, scanning the patient using a system that can perform spectral imaging; and generating a spectrum or image of an internal region of the patient. The present invention also provides a method, comprising: introducing a plurality of SACNs targeted to a molecule involved in an abnormal pathology into a patient with the abnormal pathology, wherein the SACNs become associated to a molecule associated with the abnormal pathology; and obtaining an imaging of the associated SACNs whereby an abnormal pathology may be diagnosed.

The present invention also provides a method for labeling an animal with a SACN, comprising introducing a SACN into an animal, wherein said introducing is selected from the group consisting of subcutaneous implantation, intravenous introduction.

The present invention also provides a method, comprising contacting a tissue sample with at least one biomolecule-conjugated SACN particle capable of specifically binding to the tissue sample; and (b) acquiring a Raman image of the tissue/biomolecule-conjugated SACN particles mixture.

The present invention also provides a nanoparticle, comprising a core/shell nanoparticle, at least one Raman-active reporter molecule associated with said core/shell nanoparticle, and an $SiO_2$ encapsulant.

The present invention provides a method, comprising causing deposition of a metal into a pore of a template, the pore diameter of which is less than 300 nm; causing deposition of a second material into said pore of said template, wherein the deposition of at least one of said first material and said second material involves faradaic electrochemical processes to generate a segmented, pore-bound nanoparticle; repeating the step of deposition of the metal; and releasing said second material and said template from said segmented, pore-bound nanoparticle with acid treatment to generate at least two porous free metal nanoparticles.

BRIEF DESCRIPTION OF THE FIGURES

FIG. 14A shows a TEM image of Au nanorods with 35 nm diameter released in ME. FIG. 14B shows a Raman spectrum obtained at excitation 633 nm, ME replaced with QSH.

FIGS. 15A and B show SEM images of 250 nm×250 nm Au SACNs.

FIGS. 16A and B show TEM images of a 250 nm×250 nm Au SACN.

FIG. 24A is a transmission electron micrograph of SACNs with 35 nm Au cores and 40 nm glass shells. FIG. 24B is a transmission electron micrograph of SACNs with 35 nm Au cores and 16 nm glass shells.

FIG. 25 is a transmission electron micrograph of 35 nm Au, 8 nm glass SACNs following centrifugation in a 50% glycerol solution.

DESCRIPTION OF THE INVENTION

Figure 1:
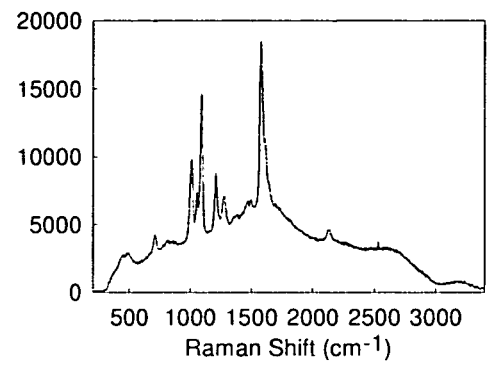
FIG. 1 shows a typical Raman spectrum.

Surface Enhanced Spectroscopy-Active Composite Nanoparticles are described in U.S. Pat. No. 6,514,767, entitled "Surface Enhanced Spectroscopy-Active Composite Nanoparticles," U.S. patent application Ser. No. 10/345,821, filed Jan. 16, 2003, entitled, "Surface Enhanced Spectroscopy-Active Composite Nanoparticles," and U.S. Patent Application No. 60/557,729, filed Mar. 29, 2004, entitled "Surface Enhanced Spectroscopy-Active Composite Nanoparticles," each of which is incorporated herein by reference.

The present invention provides new methods for the preparation of Surface Enhanced Spectroscopy-Active Composite Nanoparticles (SACNs), and methods for preparing improved SACNs. Such nanoparticles each comprise a SES-active metal nanoparticle, a submonolayer, monolayer, or multilayer of spectroscopy-active species in close proximity to the metal surface, and an encapsulating shell comprising a polymer, glass ($SiO_2$), or any other dielectric material. This places the spectroscopy-active molecule (referred to herein as the "reporter") at the interface between the metal nanoparticle and the encapsulant. In a typical embodiment, a SACN comprises (i) a metal nanoparticle core (e.g., Au or Ag), (ii) a Raman-active reporter, that gives a unique vibrational signature, and (iii) an $SiO_2$ encapsulant that "locks" the reporter molecules in place while also providing a highly compatible surface for subsequent immobilization of biomolecules. The glass coating, which is essentially SERS-inactive, also stabilizes the particles against aggregation and prevents competitive adsorption of unwanted species. In some embodiments, the reporter and the encapsulant are introduced to the nanoparticle core sequentially. In some embodiments, the encapsulant comprises the reporter molecule. In some embodiments, the SACN further comprises polymer coatings adjacent to the nanoparticle.

The nanoparticle core may be any nanoparticle known in the art. As used herein, the term "nanoparticle", "nanostructure", "nanocrystal", "nanotag," and "nanocomponent" are used interchangeably to refer to a particle, generally a metallic particle, having one dimension in the range of about 1 nm to about 1000 nm, including any integer value between 1 nm and 1000 nm. In some embodiments, the metal nanoparticle core is a spherical or nearly spherical particle of 20-200 nm in diameter. In some embodiments the range is about 2 nm to about 50 nm, in some embodiments in the range of about 20 nm to about 50 nm (for example about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nm). Anisotropic nanoparticles may have a length and a width. In some embodiments, the length of an anisotropic nanoparticle is the dimension parallel to the aperture in which the nanoparticle was produced. In the case of anisotropic nanoparticles, in some embodiments, the nanoparticle has a diameter (width) of 350 nm or less. In other embodiments, the nanoparticle has a diameter of 250 nm or less and in some embodiments, a diameter of 100 nm or less. In some embodiments, the width is between 15 nm to 300 nm. In some embodiments, the nanoparticle has a length of about 10-350 nm.

The present invention provides new methods for the preparation of Surface Enhanced Spectroscopy-Active Composite Nanoparticles (SACNs), and methods for preparing improved SACNs. Such nanoparticles each comprise a SES-active metal nanoparticle, a submonolayer, monolayer, or multilayer of spectroscopy-active species in close proximity to the metal surface, and an encapsulating shell comprising a polymer, glass ($SiO_2$), or any other dielectric material. This places the spectroscopy-active molecule (referred to herein as the "reporter") at the interface between the metal nanoparticle and the encapsulant. In a typical embodiment (for example as shown in FIGS. 24A, 24B and 25), a SACN comprises (i) a metal nanoparticle core (e.g., Au or Ag), (ii) a Raman-active reporter, that gives a unique vibrational signature, and (iii) an $SiO_2$ encapsulant that "locks" the reporter molecules in place while also providing a highly compatible surface for subsequent immobilization of biomolecules. The glass coating, which is essentially SERS-inactive, also stabilizes the particles against aggregation and prevents competitive adsorption of unwanted species. In some embodiments, the reporter and the encapsulant are introduced to the nanoparticle core sequentially. In some embodiments, the encapsulant comprises the reporter molecule. In some embodiments, the SACN further comprises polymer coatings adjacent to the nanoparticle.

Nanoparticles may be isotropic or anisotropic. Nanoparticles include colloidal metal hollow or filled nanobars, magnetic, paramagnetic, conductive or insulating nanoparticles, synthetic particles, hydrogels (colloids or bars), and the like. It will be appreciated by one of ordinary skill in the art that nanoparticles can exist in a variety of shapes, including but not limited to spheroids, rods, disks, pyramids, cubes, cylinders, nanohelixes, nanosprings, nanorings, rod-shaped nanoparticles, arrow-shaped nanoparticles, teardrop-shaped nanoparticles, tetrapod-shaped nanoparticles, prism-shaped nanoparticles, and a plurality of other geometric and non-geometric shapes. Another class of nanoparticles that has been described include those with internal surface area. These include hollow particles and porous or semi-porous particles. Moreover, it is understood that methods to prepare particles of these shapes, and in certain cases to prepare SERS-active particles of these shapes, have been described in the literature. While it is recognized that particle shape and aspect ratio can affect the physical, optical, and electronic characteristics of nanoparticles, the specific shape, aspect ratio, or presence/absence of internal surface area does not bear on the qualification of a particle as a nanoparticle.

Much of the SERS literature (both experimental and theoretical) suggests that anisotropic particles (rods, triangles, prisms) may provide increased enhancement compared to spheres. For example, the so-called "antenna effect" predicts that Raman enhancement is expected to be larger at areas of higher curvature. Many reports of anisotropic particles have been recently described, including Ag prisms and "branched" Au particles. Such anisotropic particles, used as building blocks for the formation of SACNs, are within the scope of the invention.

Anisotropic Au and Ag nanorods may be produced by electrodeposition into preformed alumina templates, in a manner similar to the production of Nanobarcodes® particles. See, for example, Nicewarner-Peña, S. R.; Freeman, R. G.; Reiss, B. D.; He, L.; Peña, D. J.; Walton, I. D.; Cromer, R.; Keating, C. D.; Natan, M. J. "Submicrometer metallic barcodes," Science 2001, 294, 137-141.; Walton, I. D.; Norton, S. M.; Balasingham, A.; He, L.; Oviso, D. F. J.; Gupta, D.; Raju, P. A.; Natan, M. J.; Freeman, R. G. "Particles for multiplexed analysis in solution: detection and identification of striped metallic particles using optical microscopy," Anal. Chem. 2002, 74, 2240-2247. These Nanobarcodes particles are prepared by the deposition of alternating layers of materials, typically Au and Ag, into preformed alumina templates. In a typical embodiment, Nanobarcodes particles are approximately 250 nm in diameter and 6 microns long.

To make metal nanoparticles to be used in SACNs, the electrodeposition may be carried out in smaller diameter pores, as described, for example, in Example 10. In some embodiments, the pore diameter is less than 100 nm and, in some embodiments, between 10 and 50 nm. Uniform alumina templates with these dimensions have been reported by several research groups. Such templates are now commercially available. Thus, in one embodiment, the invention provides a method, comprising causing deposition of a metal into a pore of a template, the pore diameter of which is less than 300 nm; causing deposition of a second material into said pore of said template, wherein the deposition of at least one of said first material and said second material involves faradaic electrochemical processes to generate a segmented, pore-bound nanoparticle; again causing deposition of a metal into the pore; and releasing the second material and the template from said segmented, pore-bound nanoparticle to generate a at least two free metal nanoparticles. In this embodiment, the pore-bound segmented nanoparticle has the composition ABA, and upon release of B and the template, two particles of A are produced. The depositions can be repeated to generate segments having the composition $(AB)_n$ or $A(BA)_n$, wherein n is any integer between 1 and 1000, and upon release from the template, n or n+1 particles of A are produced.

Figure 17A:
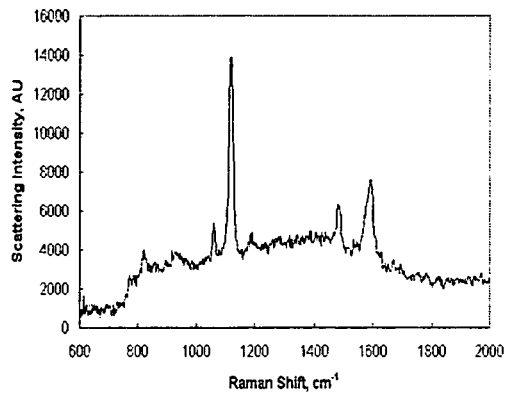
FIGS. 17A and B show Raman spectra of 250 nm×250 nm Au SACNs at 785 nm and 633 nm excitation.
Figure 17B:
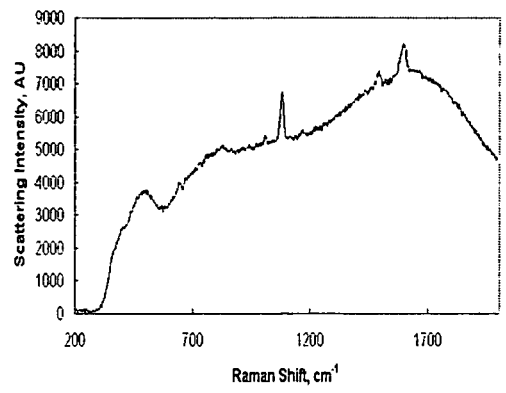

In one embodiment, SACNs prepared by this method are approximately 250 nm in diameter and 250 nm long. An example of this method is described in Example 10B. FIGS. 15A and B show a view of SACNs prepared by this method. While these particles appear to be rod-shaped, a closer view, shown in FIGS. 16A and B reveals them to have a non-geometric shape. The non-geometric shape is believed to result from the lack of a smooth interface between the metal (e.g., Au) and the material to be released (e.g., Ag) in the preparation of the particles. The lack of a smooth interface may result from interdiffusion of the two metals to form alloys, and subsequent dealloying during the release step. These non-geometric particles are useful for SERS, as shown in FIGS. 17A and B. Deliberate simultaneous deposition of Au and Ag (e.g. 80:20 Au:Ag) will lead to significant alloying, and subsequent acid-driven dissolution of Ag can lead to very highly pitted surfaces that exhibit considerable internal surface area. To the extent that reporter molecules can access such interior sites, thereby experiencing the heightened electromagnetic fields between SERS-active nanofeatures, such surfaces may exhibit improved SERS behavior.

In some embodiments, the invention provides a method comprising causing deposition of a first metal into a pore of a template, the pore diameter of which is less than 300 nm;

causing deposition of a second metal into said pore of said template; causing deposition of a third material into said pore of said template, wherein the deposition of at least one of said first material and said second material involves faradaic electrochemical processes to generate a segmented, pore-bound nanoparticle; repeating the steps of causing deposition of the first and second metals; and releasing said third material and said template from said segmented, pore-bound nanoparticle to generate at least two free metal nanoparticles, each comprising said first metal and said second metal. In this embodiment, the pore-bound segmented nanoparticle has the composition ACBAC, and upon release of B and the template, two particles of AC are produced. The depositions can be repeated to generate segments having the composition $(ACB)_n$ wherein n is any integer between 1 and 1000, and upon release from the template, n particles of AC are produced. In some embodiments, one of the metals is magnetic.

According to some embodiments, the metal includes at least one element selected from the Periodic Table of the Elements that are commonly known as metals. The metal may include primarily a single element. Alternatively, the metal may be a combination of at least two elements, such as an alloy, for example a binary alloy. Metals include Group 11 metals (Cu, Ag, and Au), or any other metals known by those skilled in the art to support SERS.

In other embodiments, the metal includes an additional component, such as in an $Au_2S/Au$ core-shell particle. $Au_2S/Au$ core-shell particles have been reported to have widely tunable near-IR optical resonance. (Averitt, et al., October 1999, JOSA B, Volume 16, Issue 10, 1824-1832.) Alternatively, Ag core/Au shell particles, like those described in J. Am. Chem. Soc. 2001, 123, 7961, or Au core/Ag shell particles, or any core-shell combination involving SERS-active metals, can be used. Other combinations suitable for use in core-shell particles are included in this invention, such as Au- or Ag-nanoparticle functionalized silica/alumina colloids, Au- or Ag-functionalized $TiO_2$ colloids, Au nanoparticle capped-Au nanoparticles (see, for example, Mucic, et al., J. Am. Chem. Soc. 1998, 120, 12674), Au nanoparticle-capped $TiO_2$ colloids, particles having and Si core with a metal shell ("nanoshells"), such as silver-capped $SiO_2$ colloids or gold-capped $SiO_2$ colloids. (See, e.g. Jackson, et al., 2004 Proc Natl Acad Sci U.S.A. 101(52):17930-5). Hollow nanoparticles such as hollow nanospheres and hollow nanocrystals may also be utilized in the SACNs. Accordingly, the present invention also provides a nanoparticle for use in a SACN comprising a core-shell particle active for SERS or a hollow nanoparticle active for SERS. The improved SERS signal of these particles may be demonstrated by manufacturing batches of these particles following a literature procedure and comparing the SERS signal to the metal particles described herein.

Methods for preparing SACNs are disclosed in U.S. Pat. No. 6,514,767. Additional methods are disclosed herein, including in the Examples section. The SACNs referred to herein are photostable (do not exhibit signal bleaching), thermally stable, show linearity of signal, and exhibit batch to batch reproducibility, as explained in Example 8.

Figure 2:
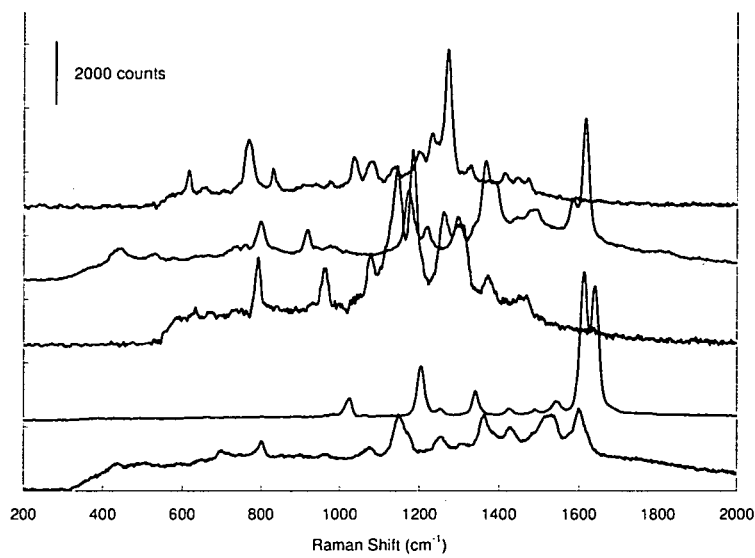
FIG. 2 shows a comparison of SACNs made with five different label molecules. From top to bottom: qunino-linethiol, malachite green isothiocyanate, mercaptobenzamidazole, bis(4-pyridyl)ethylene, Bodipy.

Examples of Raman-active reporters suitable for use in the present invention include 4-mercaptopyridine (4-MP); trans-4,4'bis(pyridyl)ethylene (BPE); quinolinethiol; 4,4'-dipyridyl, 1,4-phenyldiisocyanide; mercaptobenzamidazole; 4-cyanopyridine; 1',3,3,3',3'-hexamethylindotricarbocyanine iodide; 3,3'-diethyltiatricarbocyanine; malachite green isothiocyanate; bis-(pyridyl)acetylenes; and Bodipy. Data for 5 different reporters are shown in FIG. 2. It is clear that the spectra are distinct, and that for each species, there is at least one band that is unique. Additional features of suitable Raman-active reporters are described below.

In one embodiment, the invention provides a SACN comprising more than one reporter. The preparation of one such SACN is described in Example 3. In one embodiment, the SACN comprises a metal nanoparticle core, a trans-1,2-bis (4-pryridyl)ethylene reporter, and a 4-mercaptopyridine reporter.

There is a background signal associated with SERS substrates that is typically absent from normal Raman. The present invention also provides methods for reduction of background signal from SACNs, as well as improved SACNs exhibiting reduced background signals. In FIG. 1, for example, the background signal at 1600 $cm^{-1}$ is ~7000 counts, while the signal S is ~11,000 counts above background. If measurements are shot-noise (N) limited [$N=background^{1/2}$], the S/N=130:1, but the remaining peaks in the spectrum are significantly lower. Reducing the background by a factor of 2.25 would lead to a 50% improvement in S/N, which in turn would help to resolve weak signals and generally improve the distinctness of different spectra. The present invention therefore provides methods, comprising reducing the background signal in an assay utilizing a SACN particle, wherein said reducing comprises removing strongly SERS-active impurities from a component selected from the group consisting of the sample to be analyzed, the SACN particle, and other buffers or related materials involved in an assay. It is known that trace impurities (even those present in the reagents used to manufacture colloidal Au) may become irreversibly adsorbed to the particle surface. Accordingly, rigorous purification of all materials, and especially the reporter, using ultrafiltration, HPLC, distillation, sublimation, and/or recrystallization may reduce background signal.

Figure 3:
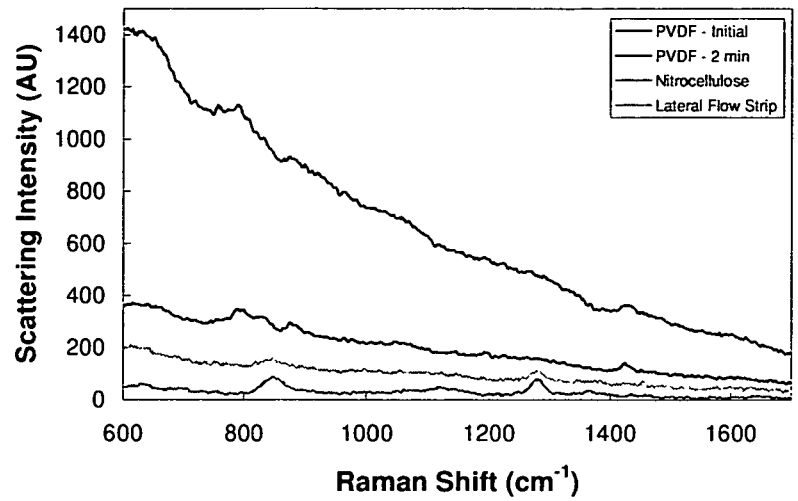
FIG. 3 shows scattering intensity vs. Raman shift for PVDF, nitrocellulose, and a lateral flow membrane.
Figure 4:
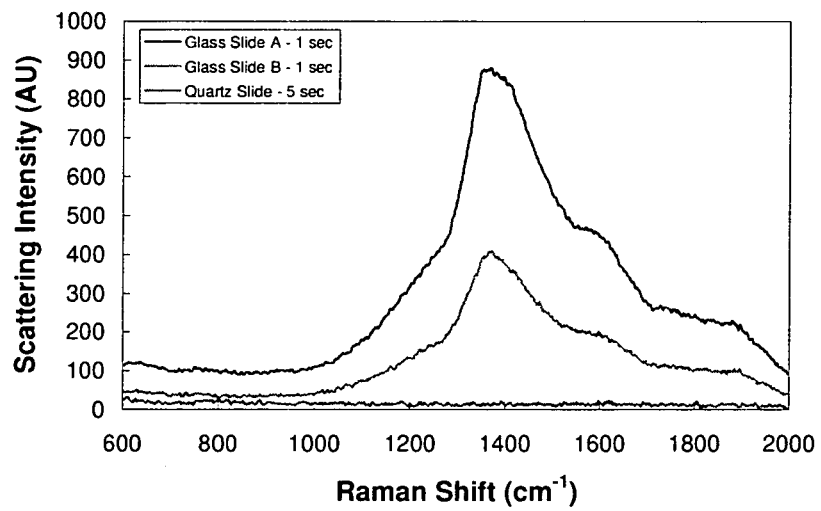
FIG. 4 shows scattering intensity vs. Raman shift for glass and quartz surfaces.

For example, in the case of a lateral flow immunoassay, common substrates are PVDF (polyvinylidene difluoride) and nitrocellulose. It has been found that nitrocellulose is desirable in terms of Raman background for two reasons. First, the PVDF exhibits some autofluorescence, as indicated by the drop in background after 2 minutes of continuous exposure to the excitation source (785 nm laser, approximately 200 mW power at the sample) in FIG. 3. Though there are few Raman features in the background, the variability in intensity is more difficult to deal with than small peaks. Even after this decrease, the overall background is larger than that obtained from two separate nitrocellulose sources, neither of which displayed photoinduced changes in Raman emission over extended illuminations. A similar phenomenon is seen in FIG. 4, which shows that glass has a weak but measurable background Raman when excited with 785 nm light. Raman spectra were acquired from glass slides obtained from two separate vendors. An integration time of 1 second was used for each acquisition, whereas a 5 second integration time was used to obtain the Raman background from a quartz slide. The quartz slide is hardly recognizable above the baseline, whereas each glass slide has measurable levels of background. Though background can be subtracted from spectra, the presence of a measurable background limits integration times and can possibly hinder detection of trace quantities of Raman reporters.

In another illustration of this effect, the background from particles made with highly purified reagents may be compared to those of identical composition made with "as-procured" reagents. Accordingly, the present invention provides a method for reduction of background signal in a Raman spectrum generated by SACNs, comprising preparing an optimized SACN, wherein said optimized SACN comprises a reporter molecule, and wherein said reporter molecule is purified prior to incorporation in the optimized SACN, and generating a Raman spectrum with said optimized SACN, wherein background signal of said spectrum is reduced compared to a spectrum generated by a corresponding SACN which is not optimized.

In some embodiments, the improved SACNs of the present invention provide an increased SERS signal when compared to known SACNs. For certain particle sizes and shapes, and at certain excitation wavelengths, Ag particles often provide larger SERS signal than Au particles. Improving the reproducibility of Au colloid synthesis would be expected to result in better SACN candidates. Accordingly, the present invention provides methods for improved Au colloid synthesis. One example of such a method is described in Example 2. This method uses a combination of $NaBH_4$, $Na_3$citrate, and $NH_2OH$ for metal reduction. The improved method is more facile and results in more monodisperse particles when compared to other methods (such as traditional synthesis of colloidal Au using just citrate as the reductant.).

In another embodiment, a nanoparticle for use in a SACN is prepared by a method comprising depositing a submonolayer coating of Ag on the surface of an Au nanoparticle, as in Freeman, et al., *Journal of Physical Chemistry* (1996), 100 (2), 718-24. It is expected that a SACN including such a coated nanoparticle can be used to increase the SERS signal from spherical nanoparticles by about two-fold.

In some embodiments, the invention provides methods for optimizing reporter loading and $SiO_2$ coating on SACNs. For each reporter successfully incorporated into a SACN, it is desirable to determine the conditions under which the maximum amount of reporter is present on the metal surface before the $SiO_2$ shell is completed.

In some embodiments, SACNs are prepared with $SiO_2$-precursor molecules that can also provide the Raman label moiety. This method should aid in increasing the SERS signal from the SACN. For example, 4-propylpyridinetrimethoxysilane may provide the Raman reporter (the pyridyl group) and act as a $SiO_2$ precursor through the trimethoxysilane. Because the $SiO_2$ precursor and the label will not have to compete for space on the Au particle, a higher surface coverage of label should be achievable. Commercially available silanes, for example, are a ready source for silanes that may be applicable as unimolecular reporters/precursors. Examples of silanes include 3-(2,4-dinitrophenylamino)propyltriethoxysilane, 2-cyanoethyltrimethoxysilane, and p-aminophenyltrimethoxysilane, n-(3-triethoxysilylpropyl)-4,5-dihydroimidazole.

In another embodiment, a nanoparticle is coated with a Raman-active polymer, such as a suitable polystyrene copolymer, a polyacetylene, or polythiophene. Such polymers may conveniently contain reactive groups, such as amines or thiols, to facilitate bioconjugation (see below) or for attachment of $SiO_2$ precursors.

In order to generate SACNs of a minimum diameter, the thickness of the $SiO_2$ may be reduced. In typical embodiments, the $SiO_2$ shell thickness ranges from 1-40 nm. In some embodiments, the $SiO_2$ encapsulant is 5-15 nm thick. While in theory it is possible to make the $SiO_2$ shell any arbitrary thickness, this may be at the expense of maintaining the integrity of the coating. In some embodiments, it is important for the $SiO_2$ shell to (i) protect the metal core and Raman label molecules from attack; (ii) prevent adsorption of potential spectral interferents on the metal surface; (iii) provide a $SiO_2$ surface for biofunctionalization: and/or (iv) prevent aggregation induced by Van der Waals forces between the metal cores.

SACNs with improved signal intensity as compared to SACNs based on spherical nanoparticles may be prepared using single crystal Au or Ag nanorods. The electrodeposition conditions (overpotential, temperature, additives, etc.) determine the structure of the nanorods that, in turn, determines the physical and mechanical properties of the nanorods. The SERS signal of nanorods can potentially be significantly increased if they are single-crystalline. It is generally known that the epitaxial, two-dimensional (2D) nucleation/growth mechanism requires electrodeposition at very low overpotential. Recently, electrodeposition of single crystalline Cu, Ag and Au nanowires was achieved with reduced metal ion concentration, low overpotential, elevated temperature and addition of surfactant to the plating solution. Wang, et al., J. Phys. Chem. B 2004, 108, 841-845; Tian, et al., Nano Lett. 2003, 3, 919-923.

Commercially available templates with pore diameters of 18 nm and 35 nm may be used to synthesize single-crystalline metal nanorods, including Au nanorods, with lengths between 50 and 100 nm. Evaporated Ag with a (111)-growth orientation and thickness of 200 nm may be used as a substrate. The electrodeposition may be conducted in potentiostatic mode by using a reference electrode to control precisely the overpotential during deposition. Significant conditions, such as solution composition and temperature, may be evaluated to achieve slow, epitaxial 2D-nucleation and growth of the Au nanorods. High-resolution TEM will reveal the nanorods' structure and X-ray diffraction may be used to determine crystal orientation. To make better use of the templates, multiple particles per pore may be manufactured by sequential plating of Au nanorods separated by thin (10-20 nm) Ag segments with the same (111)-orientation. In theory, it would be possible to completely fill a pore using this method. As the templates are typically 50-60 μm thick it would be possible to prepare more than 400 100-nm long particles per pore. The same (potentiostatic) electrodeposition technique may be applied for synthesis of Ag nanorods by using (111) Cu substrate as the selectively-etchable plating base.

Figure 5:
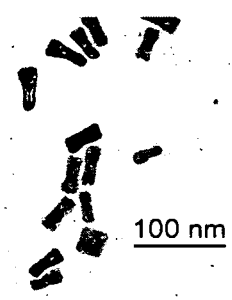
FIG. 5 shows a TEM image of nanorods prepared in a solution-based method.

As an alternative (and possibly less expensive) method, Au nanorods may be prepared using or adapting the solution-based method reported by Nikoobakht and El-Sayed. Nikoobakht, B. and El-Sayed, M. A. "Preparation and growth mechanism of gold nanorods (NRs) using seed-mediated growth method," *Chem. Mater.* 2003, 15, 1957-1962. A TEM image of nanorods prepared in a solution-based method is shown in FIG. 5. In this sample, the average nanorod is approximately 10 nm×50 nm in size, but there is considerable variation in particle size and shape, as seen by the formation of nanocubes. Solution-based methods are readily scaled to larger volumes.

In another embodiment, the present invention provides a method for reduction of background signal in a Raman spectrum generated by SACNs, comprising preparing an optimized SACN, wherein said optimized SACN is prepared by a method comprising removing material irreversibly bound to the particle surface during the course of preparing the SACN, wherein background signal of said spectrum is reduced compared to a spectrum generated by a corresponding SACN which is not optimized. In one embodiment, removal is accomplished by vigorous oxidation of the SACN intermediate followed by mild reduction. Removal may comprise treatment of the metal nanoparticle with an oxidant, such as a combination of UV-generated ozone/oxygen radicals, followed by treatment with a reductant, such as ethanol, to remove exogenous organics. An example of cleaning a SERS-active metal surface is described in: Ron, et al., *Langmuir* 1998, 14, 1116-1121. In one embodiment, the metal is Au. In the course of the method, the Au surface is converted to the unstable gold oxide, and subsequently reduced by ethanol. In another embodiment, the method comprises treatment of the metal with a combination of UV-generated ozone/oxygen radicals (the oxidant), followed by treatment with a solution of reporter in ethanol, so that adsorption of the reporter may occur immediately upon reduction. In other embodiments, the ethanol is removed by centrifugation, and the reporter added in a further step.

In some cases, species that contribute to background noise are introduced in an assay. For example, certain membranes used for filtration and preparation of samples have been found to introduce background into the Raman spectrum of assays involving SACN particles. Accordingly, in one embodiment, the present invention provides a method for reducing a background signal in a Raman spectrum of a SACN particle, comprising preparing a sample for analysis, said preparation comprising removing species from the sample or assay system that contribute to a background signal. In another embodiment, the present invention provides a method for reducing a background signal in a Raman spectrum of a SACN particle, comprising removing species from assay components that contribute to a background signal.

Uses of SACNs

The discovery of new drugs using high-throughput multiplex systems is an active research area. Automated and combinatorial chemistry can produce millions of new structures. The analysis of these drugs requires high-throughput and highly multiplex sensing. The use of SACN technology provides a highly multiplexed approach. Raman spectroscopy is ideal for providing the label-multiplex capability due to the sharpness of Raman peaks, and SERS offers many unique labeling opportunities. In some embodiments, multiplexed assays may be performed using a number of SACNs which include both a Raman-active molecule and one or more moieties. The moieties may be capable of selectively bonding to one or more detectable substances within a sample fluid, while the reporter molecules can be used to identify the SACN within the fluid (and hence the associated moiety). As the individual SACNs are relatively small, and as the number of targets which can be independently identified can be potentially quite large, large numbers of individual assays might be performed within a single fluid sample by including a large number of differing SACNs.

A typical Raman spectrum spans over 3000 cm$^{-1}$. See FIG. 1. In one embodiment, a relatively narrow region of the spectrum is focused on by generating a plurality of different SACNs that comprise structurally-related reporter molecules. For example, a set of structurally related reporter molecules might include pyridine, pyridine-d5 (deuterated pyridine), and pyridine-$^{15}$N, 4-(methylamino)pyridine, 4-aminopyridine, 4-mercaptopyridine, 4-pyridinemethanol, 4-hydroxypyridine, and 2,3,5-trimethylpyridine. Because the Raman spectrum is based upon vibration modes, small changes in chemical structure can provide unique Raman bands. Therefore, a single SERS-active structure, e.g., a nanoparticle, is modified with a plurality of structurally-related reporters to produce a plurality of SACNs, each of which has unique SERS spectra, but similar chemical reactivity. This approach may require very high spectral resolution, and therefore potentially large and/or expensive monochromators.

In another embodiment, the entire spectrum (rather than a small region thereof) is utilized. In this embodiment, a plurality of SACNs is prepared that collectively have widely-spaced vibrational bands. In some embodiments, a computer program conveniently may be used to make the selection from a given group of SACNs or reporters, each having certain spectral characteristics. In one embodiment, the computer program may be designed to select a plurality of SACNs or reporters based on user-specified spectral separation criteria. Alternatively the computer program may be designed to generate a possible SACN or reporter sets according to spectral separation magnitude. No single class of reporter molecules would be expected to exhibit vibrational bands over the entire spectral window, and therefore, in this embodiment, a variety of molecules are used as reporters. Selection of the molecules may be made guided by the following four criteria:

1. The reporter has Raman-active vibrational modes, i.e., modes causing a change in polarizability during the vibration.

2. The reporter adsorbs to any SERS-active surface, i.e., $\Delta G_{ads} << 0$.

3. The reporter has as few bands as possible, to maximize free "spectral space." Non-linear molecules with N atoms exhibit 3N-6 allowed vibrations (IR+Raman). Clearly, smaller molecules are useful, though it is necessary to balance N with $\Delta G_{ads}$, which typically is more negative for large molecules.

4. The reporter is compatible with the aqueous environment of the particle synthesis and capping protocols, as well as glass forming chemistry itself.

A wealth of tabulated information is available on Raman spectra of various molecules. See, e.g., Nakamoto, K. *Infrared and Raman Spectra of Inorganic and Coordination Compounds*; 4th Ed., John Wiley & Sons, Inc: New York; 1986; Lin-View, D.; Colthup, N. B.; Feld, M. S.; Grasselli, J. G. *The Handbook of Infrared and Raman Characteristic Frequencies of Organic Molecules*; Academic Press: San Diego, Calif.; 1991; Socrates, G. *Infrared and Raman Characteristic Group Frequencies; Table and Charts;* 3rd Ed., John Wiley & Sons, Ltd: Chichester; 2001; Workman, J., Jr. *Handbook of Organic Compounds: NIR, IR. Raman, and UV-Vis Spectra Featuring Polymers and Surfactants*; Academic Press: San Diego, Calif.; 2001; Vol. 3; Schrader, B. *Raman/Infrared Atlas of Organic Compounds;* 2nd Ed., VCH Publishers: New York, N.Y.; 1989; Hendra, P. J. and Agbenyega, J. K. *The Raman Spectra of Polymers*; John Wiley & Sons Ltd.: Chichester; 1993, all incorporated herein by reference. Using the criteria set forth above, the following classes of candidate reporters have been identified as useful for reporter molecules for SACNs.

Organic molecules: small size, unsaturation, heteroatoms, and electronegative substituents all lead to unique features. Examples with known Raman features: pyridines, triazines, pyrimidines, pyrroles, oxazoles, imidazoles, furans, cyanides, cyanamides, and their derivatives (i.e., 2-, 3-, 4-functionalized). Acetylenes, nitro/nitroso, —$CCl_2$, and —$CCl_3$ all give unique fingerprint bands. Isothiocyanates (R—N=C=S) and isocyanides (R—N≡C) are particularly attractive, since they are strong Raman scatterers, adsorb to Au, have vibrations at energies not shared by any common functional groups, and the vibrational spectra depend strongly on R-group electronegativity.

Organic/inorganic anions: extremely simple spectra (often a single peak) are a big plus. Examples of reporters that give simple spectra include cyanide, $SCN^-$, $ClO_3^-$, $HCO_2^-$, and others. Some of these may be included at the time of metal particle synthesis. For example, colloidal Au has residual tightly-bound $Cl^-$ arising from $HAuCl_4$. It is possible to start with other metal salts, especially if strong reducing agents like $NaBH_4$ are used.

Coordination complexes and other compounds containing transition metals: the metal-ligand bond is an excellent opportunity to generate vibrational features at lower Raman shifts, i.e., 200-800 cm$^{-1}$. Likewise, the ligand-based vibrations themselves are shifted relative to the uncomplexed state, and where possible, changing the metal redox state moves the energies of both bands. Ambidentate ligands like SCN⁻ are particularly attractive as they can bridge a metal ion and the metal surface. In another embodiment, complexes which contain one or more strongly SERS-active ligands (e.g. cyanide in [Fe(CN)$_6^{3-}$] or [Fe(CN)$_6^{4-}$]), or 2,2'-bipyridine (bipy) in [Ru(bipy)$_3^{2+}$]) can be used. Alternatively, organometallic species, i.e. those with one or more metal-carbon bonds (e.g. ferrocene) can exhibit intense Raman spectra.

Mixed valent species: Prussian blue and WO$_3$ are examples of materials whose vibrational spectra change as a function of metal ion redox state. The latter is particularly interesting since intercalation of H⁺ (i.e., to make H$_x$WO$_3$), D⁺, or Li⁺ allows continuous tuning.

Isotopes: Changing the reduced mass of a vibrational mode is an excellent approach to shifting its energy, and this is readily available through isotopic substitution. For example, deuterated BPE, deuterated 4,4'-dipyridyl, and deuterated bis-(pyridyl)acetylenes; as well as pyridine, pyridine-d5 (deuterated pyridine), and pyridine-$^{15}$N.

Spectral independence conveniently may be assessed using spectral deconvolution software, that combines background subtraction and peak detection, along with methods such as direct classical Least Squares. The use of such software allows the evaluation of candidate reporter molecules against other candidate reporters. Such software allows input of the pure reporter spectra and produces an output that quantitates each component in mixtures.

Once a reporter set has been selected, the signal intensity of the SACNs can be normalized, thus resulting in SACNs with equal signals per number of particles. This capability, which is not possible with molecular fluorophores, ensures the maximum possible dynamic range for a given measurement. In one embodiment, the normalization process comprises two steps. In the first step, the intensity ratios of the identifying feature for reporters are measured. In the second step, SACNs comprising a decreased quantity of reporter, defined by the inverse of its intensity ratio to that of the weakest reporter, are prepared, with the exception of the SACN comprising the lowest intensity signal. This method assumes linear adsorption at low reporter concentrations, which is routinely observed for a range of reporters (also see Example 8). In another embodiment, normalization of reporter adsorption may be achieved by increasing the amount of SiO$_2$ precursor (silane) on the nanoparticle surface during SACN synthesis, thereby reducing the reporter adsorption. These methods result in a plurality of SACNs having substantially equal peak intensities. As used herein, in some embodiments, substantially equal refers to peak intensities that are within 10% of each other. In other embodiments, substantially equal refers to peak intensities that are within 5% of each other, and in still other embodiments, substantially equal refers to peak intensities that are within 1% of each other.

The present invention comprises SACNs comprising a reactive group on the solvent-accessible part of the particle, such as an —SH group, a —NH$_2$ group, or a —COO⁻ group. In some embodiments the reactive group is associated with the encapsulent. The present invention provides methods for preparing bioconjugated SACNs, including preparation SACNs comprising a reactive group, such as thiol-active SACNs for bioconjugation. In embodiments where SACNs are encapsulated with SiO$_2$, the surface silanol groups can be derivatized. The silica shell of the SACNs can be functionalized to bear free sulfhydryl groups either during the course of making the SiO$_2$ shell ("direct modification"), or after the shell has been completely formed ("post-modification"). Many reactions for the modification of silanol groups are known to those skilled in the art. For example, the SiO$_2$ surface can be modified to present amines, (by reaction with aminopropyl trimethoxysilane (APTMS)) or ethoxides (3-glycidyloxypropyl-trimethoxysilane (GPTMS)). Reagents also exist to incorporate sulfhydryls, carboxyl and other potential sites for conjugation. Preparation of thiol-active SACNs is described in Example 4.

Thiol-active SACNs are useful for the preparation of SACNs conjugated to biomolecules, for example, peptides, proteins, and nucleic acids. For the attachment of antibodies, APTMS may be used to obtain amine groups, and subsequent carbodiimide chemistry to attach antibodies. Alternatively, GPTMS may be used to produce an ethoxide surface to which amines on the antibodies will directly react. In other embodiments, silanes terminated in alkylhalide, haloacetyl, and benzylhalide groups may be used for reaction with cysteine groups in proteins. Preparation of a bioconjugated SACN is described in Example 5. The cleanliness and presence of ions on a glass surface may have an influence on the success of derivatization.

In some embodiments, the SACNs as directly produced may be used as described herein. However, in other embodiments, better results may be obtained after the SiO$_2$ surface is "cleaned" or modified, including reactions with acids or bases.

For each method developed, the derivatizing agents (e.g. silanes) and biomolecule may be titrated in order to control levels of derivatization. Fluorescently labeled antibodies, including those many available commercially, may be used to quantitate the amount of material present on the surface. This may be monitored as variables are optimized. To determine if the biomolecule remains reactive, fluorescent dye-labeled binding partners to the biomolecule may be mixed with particles, using uncoated particles as a control. For example, streptavidin-coated SACNs can be mixed with fluorescent dye labeled-biotin. The resulting particles may be centrifuged, supernatant removed, and the fluorescence of the particles measured.

In some embodiments, biomolecules are attached to thiol-activated reporters using the heterobifunctional cross-linker sulfosuccinimidyl 4-[N-maleimidomethyl]cyclohexane-1-carboxylate (sulfo-SMCC). This molecule contains both a maleimide group that is reactive toward sulfhydryls and a sulfo-NHS ester that preferentially reacts with primary amines. In this case, a simple one-pot reaction can be used to attach streptavidin, and is readily adaptable to attachment of most proteins, amine-terminated oligonucleotides, or other molecules that bear primary amines.

SACNs with amine functionality on the surface can be treated with succinic anhydride, which reacts with primary amines to leave a free carboxylate. A carbodiimide may be used to link to amines on biomolecules, such as streptavidin. Amine-coated particles may also be linked to amines on the biomolecule using a homobifunctional linker such as glutaraldehyde. An alternative option is to first convert a portion of the protein's amines to sulfhydryls using 2-iminothiolane (Traut's reagent) and subsequently link to the particles using sulfo-SMCC.

Bioconjugated SACNs may be purified, in part for purposes of reducing non-specific binding. In the case of an antibody-conjugated SACN, free antibody will compete with the SACNs for antigens, reducing sensitivity. In one embodiment, SACNs are purified by centrifugation, including more than one centrifugation. Purification efficiency may be spectroscopically determined by doping in fluorescently labeled proteins. Because it is known than fluorescent dyes can interact with glass surfaces, it may be necessary to confirm results with radioactively labeled proteins. A tangential flow filtration device may be used for the purification of silica-coated particles as well as the purification of conjugated SACNs.

It is desirable to eliminate or reduce non-specific binding (NSB) of SACNs. The SACNs may be tested on glass slides, microwell plates and fixed cell surfaces. The level to which each of the different conjugation protocols, and surface coverage, affect NSB may be identified. For example, the effect of standard blocking agents and wash buffers, such as Tween®, and casein, in addition to different pH and buffers may be determined. In one embodiment, NSB can be reduced by blocking the particles with a blocking agent, including agents described herein. In one embodiment, the blocking agent is BSA, as described in Example 6. Alternatively NSB may be reduced or eliminated by polymer-based derivatization of the $SiO_2$ shell, such as with polyacrylamide, polyethylene glycol and dextrans, polyethylenimine and dendrimers, all known to have low NSB. In addition, commercially available microarray glass coating reagents may also be used.

In one embodiment, a conjugated SACN comprises a spacer molecule between the SACN and the conjugated biomolecule. Without being bound by theory, it is believed that certain spacer molecules, such as polyethylene glycol or dextran, will minimize NSB. Spacer molecules may be introduced into the bioconjugated SACN by methods described herein, and other methods known in the art. For example, commercially available cross-linkers that incorporate a discrete PEG subunit into a sulfo-SMCC may be used. A biomolecule may be attached to this PEG-based linker. Similarly, functional PEG molecules can be co-conjugated to SACNs along with the antibody. In this regard, the PEG acts as a spacer to minimize exposure of the bare silica surface to undesired species in the assay. Alternatively, it is possible to first conjugate bifunctional PEG molecules to the SACNs. The available functional group of the PEG may then be used for further conjugation to an antibody or other biomolecule.

In a one embodiment, assays and kits are provided in the present invention for the detection of a target analyte. An analyte can be any specific substance or component that one is desirous of detecting and/or measuring. Analytes of interest include, for example, antigens (such as antigens specific to bacterial, viral or protozoan organisms); antibodies, including those induced in response to an infection, allergic reaction, or vaccine: hormones, proteins and other physiological substances (for example, human chorionic gonadotropin, estrogens, progestins, testosterones, corticosteroids, human growth factors, hemoglobin, and cholesterol); nucleic acids; a variety of enzymes; therapeutic compounds and illicit drugs; contaminants and environmental pollutants; or any number of natural or synthetic substances.

In one embodiment, the invention provides a sandwich immunoassay using SACNs that can be used to replace an ELISA-type assay. The analytical technique of enzyme-linked immunoadsorbant assay (ELISA) and related techniques are now the most widely known immunoassays. The stages of a conventional ELISA procedure generally include initially adsorbing a capture antibody onto a solid support. Upon incubation with a sample, an antibody-target protein complex is formed. The final sandwich immunoassay complex typically includes an indicator enzyme that permits optical measurements of the antigen concentration. In a sandwich assay immunoassay using SACNs, however, instead of an indicator enzyme, a SACN is used to permit optical detection. In this embodiment, the bioconjugated SACNs may be prepared with precisely known concentrations of specific active antibody species attached to their surfaces, and can be quantified using a binding assay with a protein quantification assay, such as the BCA assay. Such an assay can be multiplexed, as described in Example 11.

Figure 20:
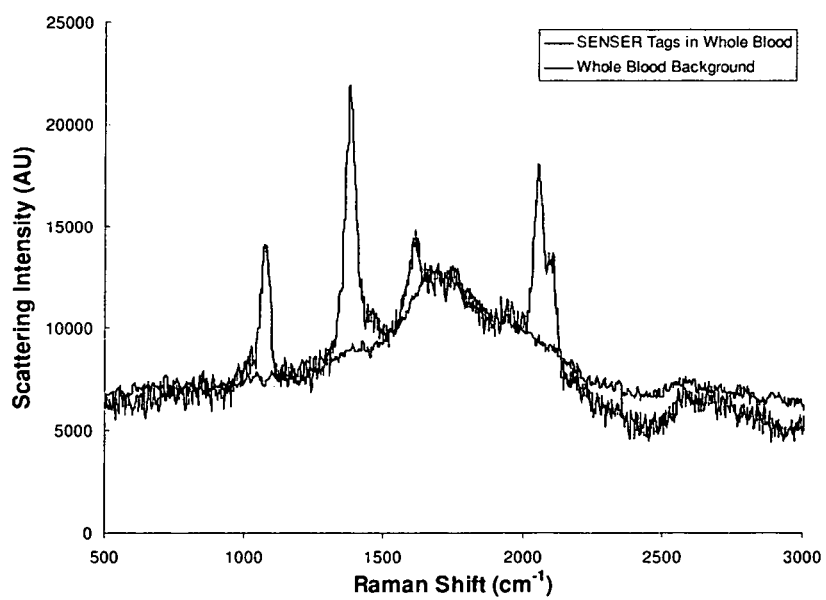
FIG. 20 shows scattering intensity vs. Raman shift at 758 nm excitation for whole blood without and with SACNs.

The methods according to the present invention are useful for detection of analytes in samples of biological origins. Such samples include, but are not limited to blood or serum; saliva, sputum, tears, sweat, or other secreted fluids; urine or fecal matter; as well as biologically derived fluids such as cerebrospinal fluid, interstitial fluid, cellular extracts and the like. Whole blood is a suitable medium for SERS measurements from SACNs. See FIG. 20.

A minimal volume of sample is used for the assay, including sample volumes that range from about 1 µL to about 500 µL in some embodiments, from about 1 µL to about 100 µL in other embodiments, from about 5 µL to about 50 µL in other embodiments, and between about 10 µL and about 30 µL in still other embodiments. Larger sample volumes may be used if the situation warrants it, such as in the case of bulk blood monitoring in a blood bank, where sample volumes may be on the order of milliliters. Smaller volumes may also be used if the situation warrants; for example, in the case of an assay for a cell, the volume of the cell may be used. In the case of an assay that targets an intracellular component, the volume of the intracellular component may be used. In such cellular or subcellular assays, the volume may be as low as 1 pL.

The assays of the present invention are based on binding assays such as, but not limited to, immunoassays. The binding partners involved in such binding assays include, but are not limited to, the following binding pairs: antibody and antigen or hapten; hormone and receptor; biotin and avidin; carbohydrate and lectin; effector and receptor molecules; enzymes and cofactors, substrates, or inhibitors; aptamers and their targets, and complementary nucleotide sequences. Thus, the descriptions and examples included below are for demonstration purposes and should not be considered limiting to the particular applications addressed.

In one, embodiment, the present invention comprises a method for detecting the presence of at least one analyte which comprises the following steps: (a) contacting the sample suspected of containing the analyte with at least one specific binding partner to the analyte on a lateral-flow assay surface to bind to the analyte in the sample; (b) previously, simultaneously or subsequently to step (a), binding the at least one analyte binding partner with a SACN to form a conjugated SACN; and (c) detecting a SERS signal whereby the presence of the analyte is determined in the sample by the intensity or presence of the signal.

In one embodiment, the sample is placed on a sample zone. The sample filters down through the sample zone and then through a label zone containing a label, e.g., a conjugated SACN. The SACN binds to sample analyte to form complexes, and the complexes then migrate along the membrane or detection strip. The complexes of SACN-analyte, if present, bind to the at least one specific binding partner that is immobilized in a detection zone on the membrane. Formation of this SACN-labeled complex with its specific binding partner results in a detectable SERS signal, indicating a positive result that the analyte is present in the sample. In the case where the analyte is IL-5, for instance, the SACN may be conjugated to an IL-5 antibody and a corresponding capture antibody for IL-5 may be present in the detection zone. A lateral flow assay is described in Example 12.

In one embodiment, the biological sample is a cell. The cell may either be living or dead. Images of cells containing Raman spectral information can be obtained by a number of methods. A microscope can be coupled to a CCD camera such that complete images of the object may be obtained. Then, between the sample and the camera, a wavenumber filtering device such as a monochromator or liquid crystal tunable filter is inserted. The filtering device only allows a narrow bandwidth of the scattered radiation to reach the camera at any one time. Multiple images are collected, each covering a small spectral range of the scattered radiation. The spectra from each point in the image are assembled in software. At the other extreme, light from a single point of an image may be dispersed through a monochromator and the complete spectrum of that point can be acquired on an array detector. The object is then scanned such that each point in the image is acquired separately. The Raman image is then assembled in software. In another approach, a line scan instrument can be constructed that excites the sample with a line of radiation. The line is imaged spatially along one axis of a CCD camera while simultaneously being spectrally dispersed along the orthogonal axis. Each readout of the camera acquires the complete spectrum of each spatial pixel in the line. To complete the image the line is scanned across the sample.

Thus, according to this invention, cells or cell populations may be identified by using an antibody-conjugated SACN prepared with an antibody which binds a cell surface antigenic receptor which is expressed on a cell subpopulation. Identification of cells and cell populations may also be achieved via a sandwich approach. For example, Example 13 describes an assay in which NeutrAvidin conjugated SACNs were applied to SK-BR-3 cells stained for the Her2 receptor and biotinylated anti-mouse antibody. Novel high-throughput cell-based screening technologies are needed to keep pace with growing compound libraries and the almost daily discovery of new therapeutic targets. For example, Vitra Biosciences CellPlex™ card allows for multiplexing of cellular assays. Another approach, which would allow for versatility in the assay formats, is to encode cells with unique identifiers. This would allow populations of cells to be studied simultaneously, thereby increasing throughput. For example, cell type A can be encoded with SACN type 1, cell type B encoded with SACN type 2, and so forth. These cells can be mixed together prior to the cellular assay being performed. The cellular assay would be performed using traditional fluorescence methods, such as GFP. Final analysis would be completed by reading the fluorescence to determine the outcome of the experiment, and SERS to decode the cell type, using a Raman microscope or cell sorted with Raman detection. This strategy would allow the study of phenotypes in mixed cell populations.

SACNs may also be used to detect intracellular targets. SACNs may be introduced into cells via microinjection, electroporation, endocytosis-mediated approaches including the use of amphipathic peptides such as PEP-1, the use of cationic lipid-based reagents, such as Lipofectamine (Invitrogen), and the use of micelles and transfection reagents such as transferrin, mannose, galactose, and Arg-Gly-Asp (RGD), and other reagents such as the dendrimer-based reagent SuperFect (Qiagen). Intracellularly, indirect methods can be used to prove that the particles are bound to the desired targets. The simplest method to demonstrate the specificity of the probes is to use immunofluorescence to verify the location of the SACNs. There are a number of commercially available fluorescent probes that are useful for labeling cellular structures (such as the mitochondria, Golgi apparatus and endoplasmic reticulum) in living cells. By conjugating an antibody that targets the same structure, what fraction of particles is actively labeling their target can be determined; and what percentage are non-specifically bound. Another approach to verifying the location of the SACNs is to use fluorescent protein fusions, such as GFP and its analogs.

The present invention is directed to imaging agents displaying important properties in medical diagnosis. More particularly, the present invention is directed to imaging agents comprising SACNs. The imaging agents of the present invention are useful in imaging a patient generally, and/or in specifically diagnosing the presence of diseased tissue in a patient. By choice of composition, the excitation and emission of SACNs can be tuned to occur between 633 nm and 1000 nm, in the minimum region for absorption and scattering by tissues. The imaging process may be carried out by administering an imaging agent of the invention to a patient, and then scanning the patient using any system that can perform spectral imaging, such as spot scanning confocal microscopes, line scanning systems, and Optical Coherence tomographic systems. SACNs of the present invention can also be seen by any imaging system that detects only over a single wavelength band, the list above as well as any fluorescence imaging system that has an excitation light source and filtered image detection. Other suitable imaging systems and methods are described in HANDBOOK OF OPTICAL AND BIOMEDICAL DIAGNOSTICS, Valery Tuchin editor (2004) Springer. Also included are time domain methods, such as dynamic light scattering spectroscopy and tomography, time-of-flight imaging, quasi-elastic light scattering spectroscopy, photon-correlation spectroscopy, Doppler spectroscopy, and diffusion wave spectroscopy. All these techniques allow differentiation between photons and where they have been based on their time signatures. Since SACNs will have different time signatures than fluorescent substances, etc., they can be discriminated against tissues and other labels with these methods. Useful instrument parameters are a modulated light source and time sensitive detector. Modulation can be pulsed or continuous.

The scanning results in spectra or images of an internal region of a patient and/or of any-diseased tissue in that region. By region of a patient, it is meant the whole patient, or a particular area or portion of the patient. The imaging agent may be employed to provide images of the vasculature, heart, liver, and spleen, and in imaging the gastrointestinal region or other body cavities, or in other ways as will be readily apparent to those skilled in the art, such as in tissue characterization, blood pool imaging, etc.

This invention also provides a method of diagnosing abnormal pathology in vivo comprising, introducing a plurality of SACNs targeted to a molecule involved in the abnormal pathology into a bodily fluid contacting the abnormal pathology, wherein the SACNs become associated to a molecule involved in the abnormal pathology, and imaging the associated SACNs in vivo. The method is generally applicable to any organ accessible by the probes: gastro-intestinal tract, heart, lung, liver cervix, breast, etc. In some embodiments, the SACNs can be introduced via an endoscope, as in the case of a colonoscopy, or a needle, or used with a disposable tip or sleeve. In other embodiments, the SACNs may be introduced by directly by the imaging probe itself. For example, individual optical fibers, or bundles of optical fibers, can be introduced into live organisms for imaging, and has been demonstrated for imaging of nerves, brain, microvessels, cells, as well as for characterizing biodistribution. Gel-coated optical fibers are very well known in the sensor literature. SACNs can be non-covalently bound to the gel, diffusing into the relevant tissue upon introduction. A variety of other methods to immobilize SACNs onto the outer surface of fibers such that they diffuse into liquid phases to which they are contacted can be envisioned.

In one embodiment, the present invention provides a method for labeling an animal with a SACN, comprising introducing a SACN into an animal. SACNs can be introduced into animals by any suitable means, such as by subcutaneous implantation or intravenously, and detected using appropriate equipment (see 15). The present invention also provides an identification system and related methods for animals such as livestock or house pets by utilizing a SACN implanted under the hide or skin to identify the animal.

It should be noted that the foregoing description is only illustrative of the invention. Various alternatives and modifications can be devised by those skilled in the art without departing from the invention. Accordingly, the present invention is intended to embrace all such alternatives, modifications and variances which fall within the scope of the disclosed invention.

For completeness, various aspects of the invention are set out in the following numbered clauses:

1. A method, comprising:
   a) causing deposition of a metal into a pore of a template, the pore diameter of which is less than 300 nm;
   b) causing deposition of a second material into said pore of said template, wherein the deposition of at least one of said first material and said second material involves faradaic electrochemical processes to generate a segmented, pore-bound nanoparticle;
   c) repeating step a); and
   d) releasing said second material and said template from said segmented, pore-bound nanoparticle to generate at least two free metal nanoparticles.
2. The method of clause 1, wherein said free metal nanoparticle has a length from 10-300 nm and a width from 15-300.
3. The method of clause 1, further comprising repeating step b) and c).
4. The method of clause 1, wherein said template is alumina.
5. The method of clause 1, wherein the second material is a metal.
6. The method of clause 5, wherein the second material Ag.
7. The method of clause 1, wherein said metal is Au.
8. The method of clause 4, wherein said second material is Ag.
9. The method of clause 8, wherein said template is alumina.
10. The method of clause 1, wherein said releasing comprises treating with a strong acid followed by a strong base.
11. The method of clause 10, wherein said strong acid is nitric acid and said strong base is NaOH.
12. The method of clause 1, wherein said electrodeposition is selected from the group consisting of pulse plating, pulse current plating, reverse pulse current plating, and double pulse plating.
13. The method of clause 1, further comprising providing a short SAM-molecule during step c).
14. The method of clause 1, wherein said releasing comprises using a solution providing a SERS-active molecule.
15. A method, comprising:
   a) causing deposition of a metal into a pore of a template, the pore diameter of which is less than 300 nm;
   b) causing deposition of a second material into said pore of said template, wherein the deposition of at least one of said first material and said second material involves faradaic electrochemical processes to generate a segmented, pore-bound nanoparticle;
   c) repeating step a); and
   d) releasing-said second material and said template from said segmented, pore-bound nanoparticle with acid treatment to generate at least two porous free metal nanoparticles.
16. A method, comprising:
   a) causing deposition of a first metal into a pore of a template, the pore diameter of which is less than 300 nm;
   b) causing deposition of a second metal into said pore of said template:
   c) causing deposition of a third material into said pore of said template, wherein the deposition of at least one of said first material and said second material involves faradaic electrochemical processes to generate a segmented, pore-bound nanoparticle;
   d) repeating steps a) and b); and
   e) releasing said third material and said template from said segmented, pore-bound nanoparticle to generate a at least two free metal nanoparticles, each comprising said first metal and said second metal.
17. The method of clause 16.
18. The method of clause 16, wherein said second metal is magnetic.
19. A method, comprising:
   preparing an optimized SACN, wherein said optimized SACN is prepared by a method comprising removing material irreversibly bound to the particle surface during the course of preparing the SACN, wherein background signal of said spectrum is reduced compared to a spectrum generated by a corresponding SACN which is not optimized.
20. The method of clause 19, wherein said removal comprises the steps of:
   a) oxidation and
   b) reduction.
21. The method of clause 20, wherein said oxidation comprise contacting the SACN with UV-generated ozone/oxygen radical.
22. The method of clause 20, wherein said reduction comprises contacting the SACN with ethanol.
23. The method of clause 22, wherein said solution of reporter in ethanol, so that adsorption of the reporter may occur immediately upon reduction. In other embodiments, the ethanol is removed by centrifugation, and the reporter added in a further step.
24. A method, comprising
   reducing the background signal in an assay utilizing a SACN particle, wherein said reducing comprises removing impurities from a component selected from the group consisting of the sample to be analyzed, the SACN particle, and the assay vessel.
25. A method, comprising
   a) preparing a plurality of SACN particles, each comprising a different Raman reporter;
   b) measuring the intensity ratio of the Raman reporters; and
   c) preparing a second plurality of SACN particles having the intensities of the reporters normalized to that of the reporter that has the weakest intensity,
   whereby a plurality of SACNs having substantially equal peak intensities in a Raman spectrum are prepared.
26. The method of clause 25, wherein the intensities of the reporters are normalized by preparing SACNs with a decreased quantity of reporter, wherein the decreased quantity is defined by the inverse of the intensity ratio of that reporter to that of the weakest reporter.
27. The method of clause 25, wherein the intensities of the reporters are normalized by preparing SACNs with an increased quantity of silane, wherein the increased quantity is defined by the inverse of the intensity ratio of that reporter to that of the weakest reporter.

28. A SACN, comprising a nanoparticle core, a Raman-active reporter molecule, an SiO2 encapsulant, and a reactive group selected from the group consisting of an —SH group, a —NH2 group, and a —COO— group.

29. A method, comprising
 a) providing a nanoparticle;
 b) associating a Raman-active reporter molecule with said nanoparticle;
 c) encapsulating the nanoparticle with SiO2; and
 d) modifying the SiO2 to bear a reactive group selected from the group consisting of an —SH group, a —NH2 group, and a —COO— group,
 whereby an activated SACN is prepared.

30. The method of clause 29, wherein the modifying comprises modifying during the encapsulating step.

31. The method of clause 29, wherein the modifying comprises modifying after the encapsulating step.

32. The method of clause 29, wherein the modifying comprises modifying to present amines.

33. The method of clause 32, wherein the modifying is accomplished by reaction with aminopropyl trimethoxysilane (APTMS)) or ethoxides (3-glycidyloxypropyl-trimethoxysilane (GPTMS)).

34. The method of clause 29, further comprising attaching a biomolecule to said activated SACN, whereby a bioconjuated SACN is prepared.

35. The method of clause 34, wherein the biomolecule is selected from the group consisting of a protein and a nucleic acid.

36. The method of clause 34, wherein said attaching comprises reacting said activated SACN and said biomolecule through a compound selected from the group consisting of a heterobifunctional cross-linker, sulfosuccinimidyl 4-[N-maleimidomethyl]cyclohexane-1-carboxylate, succinic anhydride, a carbodiimide, a homobifunctional linker, glutaraldehyde, 2-iminothiolane, and a combination of any of the foregoing.

37. The method of clause 34, further comprising purifying the bioconjuated SACN.

38. The method of clause 37, wherein the purifying is selected from the group consisting of centrifugation and tangential-flow filtration.

39. The method of clause 34, further comprising attaching a spacer molecule to the bioconjugated SACN, wherein the spacer molecule is between the nanoparticle and the biomolecule.

40. The method of clause 39, wherein the spacer molecule is selected from the group consisting of polyethylene glycol and dextran.

41. A bioconjuated SACN, comprising:
 a) a nanoparticle
 b) a Raman-active reporter molecule associated with said nanoparticle
 c) an SiO2 encapsulant; and
 d) a biomolecule selected from the group consisting of a protein and a nucleic acid.

42. The bioconjugated SACN of clause 41, wherein said protein is an antibody.

43. The bioconjugated SACN of clause 41, further comprising a spacer molecule between the nanoparticle and the biomolecule.

44. The bioconjugated SACN of clause 43, wherein the spacer molecule is selected from the group consisting of polyethylene glycol and dextran.

45. A method for detecting an analyte comprising:
 a) obtaining a biological sample; and
 b) contacting the sample with a bioconjugated SACN comprising a biomolecule that binds to the analyte; and
 c) detecting the analyte bound to said bioconjugated SACN.

46. The method of clause 45, herein the biomolecule is an antigen, and the analyte is an antibody.

47. The method of clause 45, wherein the biomolecule and the analyte are peptides or proteins.

48. The method of clause 45 wherein the biomolecule and the analyte are independently selected from a hormone and a receptor.

49. The method of clause 45 wherein the biomolecule and the analyte are independently selected from biotin and avidin.

50. The method of clause 45 wherein the biomolecule and the analyte are independently selected from carbohydrate and lectin.

51. The method of clause 45 wherein the biomolecule and the analyte are independently selected from effector and receptor molecules.

52. The method of clause 45 wherein the biomolecule and the analyte are independently selected from enzymes and a member of the group selected from the group consisting of cofactors, substrates, and inhibitors.

53. The method of clause 45 wherein the biomolecule and the analyte are complementary nucleotide sequences.

54. The method of clause 45, wherein the sample is selected from the group consisting of blood, serum, saliva, sputum, tears, sweat, another secreted fluid; urine, fecal matter; cerebrospinal fluid, interstitial fluid, a cellular extract, and a cell.

55. A method, comprising,
 a) contacting a sample suspected of containing an analyte with at least one specific binding partner to the analyte on a lateral-flow assay surface to bind to the analyte in the sample;
 b) previously, simultaneously or subsequently to step (a), binding at least one analyte binding partner with a SACN; and
 c) detecting a SERS signal whereby the presence of the analyte is determined in the sample by the intensity or presence of the signal, whereby the presence of at least one analyte in the sample is determined.

56. A method, comprising:
 a) providing a microscope coupled to a CCD camera;
 b) providing a cell;
 c) contacting the cell with at least one SACN capable of specifically binding to the cell or a portion of the cell;
 d) providing a wavenumber filtering device between the cell and the camera
 e) acquiring a plurality of data sets; and
 f) assembling the data sets;
 whereby a spatial profile of the SACN is acquired.

57. The method of clause 56, wherein the wavenumber filtering device is selected from the group consisting of a monochromator, a notch filter, a filter wheel, acousto-optic tunable filter, Fourier transform interference filter, a liquid crystal tunable filter, and combinations of the foregoing.

58. The method of clause 56, wherein said wavenumber filtering device comprises a liquid crystal tunable filter, and said acquiring comprises:
 a) acquiring data at a first frequency; and
 b) optionally acquiring data at a second and subsequent frequencies.

59. The method of clause 56, wherein said acquiring comprises:
 a) dispersing light from a single point of a location through a monochromator;

b) acquiring the complete Raman spectrum of that point on an array detector; and c) repeating a) and b) multiple locations.

60. The method of clause 56, wherein said acquiring comprises:

a) exciting the sample with a line of radiation;

b) acquiring the complete spectrum of each spatial pixel in the line; and c) scanning the line across the sample.

61. A nanoparticle, comprising:

a) a metal nanoparticle;

b) more than one Raman-active reporter molecule associated with said nanoparticle; and c) an SiO2 encapsulant.

62. The nanoparticle of clause 61, wherein the more than one Raman-active reporter molecule comprises 4-mercaptopyridine and trans-4,4'bis(pyridyl)ethylene.

63. A nanoparticle, comprising:

a) a core/shell nanoparticle;

b) at least one Raman-active reporter molecule associated with said core/shell nanoparticle; and c) an SiO2 encapsulant.

64. The nanoparticle of clause 63, further wherein said core/shell nanoparticle is selected from the group consisting of an Au2S core/Au shell particle, an Ag core/Au shell particle, silica core/Au shell particles, silica core/Ag shell particles, alumina core/Au shell particles, alumina core/Ag shell particles, TiO2 core/Au shell particles, and TiO2 core/Ag shell particles.

65. A method, comprising, a) contacting HAuCl4 with hydroxylamine hydrochloride;

b) further contacting the solution resulting from step a) with a mixture of sodium citrate dehydrate and NaBH4, whereby a gold nanoparticle is produced.

66. A method comprising, a) providing a gold nanoparticle prepared by the method of clause 65;

b) associating a Raman-active reporter molecule with said nanoparticle; and c) encapsulating the nanoparticle with SiO2; whereby a SACN is prepared.

67. A nanoparticle comprising:

a) a anisotropic metal nanoparticle;

b) a SERS-active reporter molecule associated with said anisotropic metal nanoparticle;

c) SiO2 encapsulating the anisotropic metal nanoparticle.

68. The nanoparticle of clause 67, wherein the anisotropic metal nanoparticle has a shape selected from the group consisting of a spheroid, rod, disk, pyramid, cube, cylinder, nanohelix, nanospring, nanoring, rod-shaped nanoparticle, arrow-shaped nanoparticle, teardrop-shaped nanoparticle, tetrapod-shaped nanoparticle, prism-shaped, porous, and non-geometric shaped nanoparticle.

69. The nanoparticle of clause 68, wherein the nanoparticle is non-geometric shaped, and approximates a nanorod.

70. The method of clause 69, wherein the nanoparticle has a diameter of about 250 nm and length of about 250 nm.

71. A method comprising, a) administering a SACN nanoparticle imaging agent to a patient, b) scanning the patient using a system that can perform spectral imaging; and c) generating a spectrum or image of an internal region of the patient.

72. The method of clause 71, wherein said system is selected from the group consisting of a spot scanning confocal microscope, a line scanning system, an Optical Coherence tomographic system, a system that detects only over a single wavelength band, a fluorescence imaging system comprising an excitation light source and filtered image detection.

73. The method of clause 71, wherein the region of a patient is selected from the group consisting of the whole patient, the vasculature, heart, liver, and spleen, the gastrointestinal region.

74. The method of clause 71, wherein the system that can perform spectral imaging is a portable system.

75. A method, comprising:

a) introducing a plurality of SACNs targeted to a molecule involved in an abnormal pathology into a patient with the abnormal pathology, wherein the SACNs become associated to a molecule associated with the abnormal pathology; and b) obtaining an imaging of the associated SACNs, whereby an abnormal pathology may be diagnosed.

76. The method of clause 75, wherein said the location of the abnormal pathology comprises the gastro-intestinal tract, heart, lung, liver cervix, breast, and colon.

77. The method of clause 71, wherein said SACN is non-covalently associated with an imaging probe, wherein said administering comprises introducing the imaging probe, and wherein said SACNs disassociate into the tissue or a bodily fluid.

78. A method for labeling an animal with a SACN, comprising introducing a SACN into an animal, wherein said introducing is selected from the group consisting of subcutaneous implantation, intravenous introduction.

79. The method of clause 78, further comprising detecting the SACN or labeled animal.

80. A method, comprising:

(a) contacting a tissue sample with at least one biomolecule-conjugated SACN particle capable of specifically binding to the tissue sample; and (b) acquiring a Raman image of the tissue/biomolecule-conjugated SACN particles mixture.

81. The method of Clause 80, where the tissue is contacted with one or more additional non-SACN reagents.

82. The method of Clause 81, where the additional reagent is selected from the group consisting of eosin, hemotoxylin, and a combination of hemotoxylin and eosin.

83. The method of clause 80, further comprising:

(a) acquiring a background Raman image of a tissue sample prior to step (a) of clause 80; and (b) subtracting the background spectrum from the Raman image of the tissue/biomolecule-conjugated SACN particles mixture acquired in step (b) of clause 80.

84. The method of Clause 83, where the tissue is contacted with one or more additional non-SACN reagents.

85. The method of Clause 83, where said additional reagent is selected from the group consisting of eosin, hemotoxylin, and a combination of hemotoxylin and eosin.

86. The method of clause 80, further comprising comparing the Raman image with an image of a tissue sample which has been stained with strongly colored organic dyes to visualize cell size and shape.

EXAMPLES

Example 1

A typical synthesis of ~45 nm diameter Au colloid using a combination of sodium borohydride, sodium citrate, and hydroxylamine hydrochloride is described. All glassware are washed with aqua regia and rigorously rinsed with 18 MΩ water. The reactions are carried out in a cold room. Solutions of 0.01% (w/w) $HAuCl_4 \cdot 3H_2O$ in water, 8% (w/w) sodium citrate dihydrate in 0.01 N NaOH, $10^{-4}$% sodium borohydride in 0.01 N NaOH, and 400 mM hydroxylamine hydrochloride in water, are prepared. A mixture of citrate and borohydride solutions is then prepared by combining 1 mL of the sodium citrate solution with 100 µL of the sodium borohydride solution and 500 µL of 0.01 N NaOH. After preparing this mixture 200 µL of the hydroxylamine solution is injected into 100 mL of the HAuCl$_4$ solution in a 250 mL Erlenmeyer flask, and briefly stirred. After 20 minutes the borohydride/citrate mixture is injected into the rapidly stirring solution of HAuCl$_4$ and hydroxylamine. Best results are obtained when the mixture is injected midway between the center of the stirring vortex and the wall of the flask.

Example 2

Preparation of Gold Nanoparticles. Stock solutions of HauCl$_4$.3H$_2$O are prepared at either 1% or 2% concentration (w/v) in H$_2$O. These solutions are filtered through 0.2 µm membranes before being placed in the cold room. The bottles containing the stock solutions are also typically covered in aluminum foil to reduce exposure to light. The following solutions are typically prepared:
1. 1.0 L of 0.02% HauCl$_4$ in H$_2$O.
2. 5 mL 32% (w/v) sodium citrate dehydrate in 0.01 N NaOH.
3. 10 mL 1.6 M hydroxylamine hydrochloride in H$_2$O.
4. 10 mL of 4% (w/v) NaBH$_4$ in 1.0 N NaOH which is prepared by dilution of the stock solution.

All reactions are carried out in a cold room after allowing solutions to reach the temperature of the room. The HauCl$_4$ solution is placed in a 2 L round bottom flask and a glass stirring rod with Teflon paddle is inserted into the flask to provide stirring. 1.0 mL of the hydroxylamine solution is added to the flask and stirred. Immediately after the addition of the hydroxylamine a solution of $4 \times 10^{-4}$% NaBH$_4$ is prepared by serial dilution of the 4% stock. These dilutions are made in 0.01N NaOH. Then, 1 mL of 32% sodium citrate is mixed with 525 µL of 0.01 N NaOH and 75 µL of $4 \times 10^{-4}$% NaBH$_4$. At 20 minutes after the addition of hydroxylamine 1.0 mL of the citrate/borohydride mixture is added to the reaction flask while it is being stirred rapidly.

Example 3

SERS Spectra of SACNs Tagged with Both 4-mercaptopyridine (4-MP) and trans-4,4'-bis(pyridyl)ethylene (BPE)

Materials:
Water used for all preparations was 18.2 MΩ, distilled through a Barnstead nanopure system. 3-aminopropyltrimethoxysilane (APTMS), HAuCl$_4$.3H$_2$O, trisodium citrate dihydrate, sodium hydroxide, sodium borohydride, hydroxylamine hydrochloride, trans-1,2-bis(4-pyridyl)ethylene (BPE), 4-mercaptopyridine, sodium silicate, tetraethyl orthosilicate (TEOS), ethyl alcohol, and 2.0 M ammonia in ethanol were obtained from Sigma-Aldrich. BPE was recrystallized before use.

Colloid Preparation:
35-nm colloidal Au was prepared from HAuCl$_4$.3H$_2$O. Aqueous solutions of 4% sodium citrate and 400 mM hydroxylamine hydrochloride were prepared immediately prior to synthesis, as was a solution of $10^{-2}$% sodium borohydride in 0.001 N NaOH. A 300 µL aliquot of this borohydride solution was mixed with 500 µL of the citrate and 350 µL of the hydroxylamine and immediately injected into 200 mL of 0.01% HAuCl$_4$ under vigorous stirring. The size of the resulting particles was determined by transmission electron microscopy using ImageJ software.

SACNs Preparation:
All reactions were performed in plastic flasks. A typical experiment used 30 ml of 35-nm colloid. The colloid was rendered vitreophilic with the addition 40 µL of 1.0 mM APTMS and allowed to stir for 15 minutes. The Raman label mixture (600 µL of $10^{-5}$ M 4-mercaptopyridine and 50 µL of $10^{-5}$ M BPE) was added to the solution, which was then stirred for 15 additional minutes. Finally, 1.2 mL of 0.54% sodium silicate was added and allowed to react for 42 hours. After this time 120 mL of EtOH was added to the solution, followed by 1 mL of 2 M ammonia (in ethanol) and 20 µL of tetraethylorthosilicate (TEOS). This reaction was allowed to proceed for 1 day before purifying via centrifugation. This amount of TEOS varied, if a thinner or thicker shell is desired.

Figure 6:
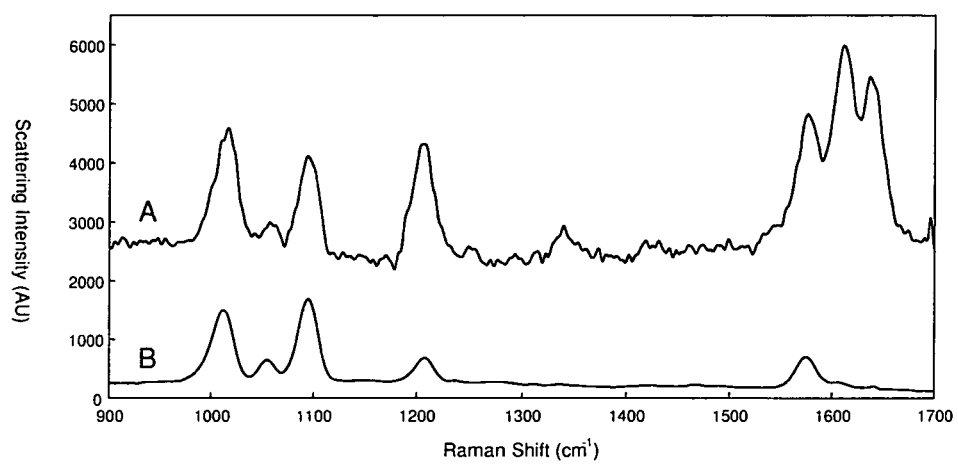
FIG. 6 shows SERS spectra of 4-MP/BPE-SACNs obtained using 633 nm excitation (Trace A) and 785 nm excitation (Trace B).
Figure 7:
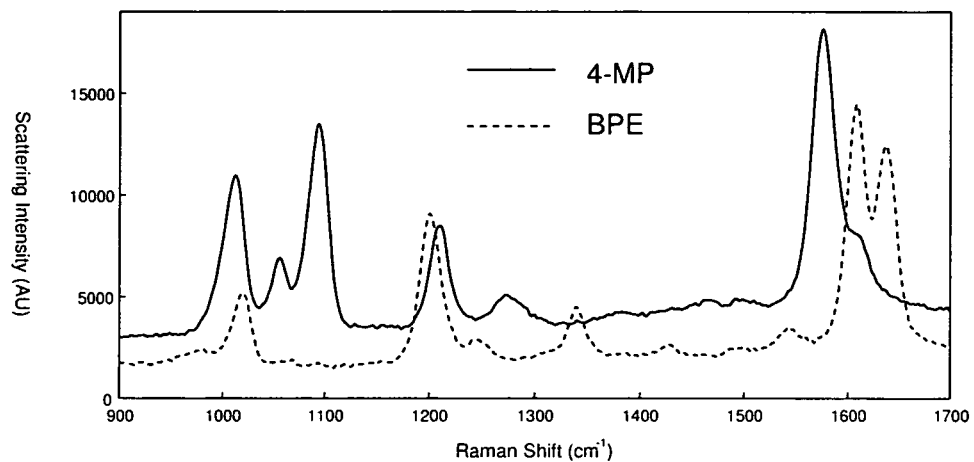
FIG. 7 shows Raman spectra of BPE-SACNs (dashed line) and 4 MP SACNs (solid line).

The resulting SACNs had a mixture of two different species of Raman-active molecules, 4-MP and BPE, in a 12:1 ratio. SERS spectra of these 4-MP/BPE-SACNs obtained using 633 nm excitation (Trace A) and 785 nm excitation (Trace B) are plotted in FIG. 6. For comparison, the characteristic Raman spectra of BPE-SACNs (dashed line) and 4-MP-SACNs (solid line) are plotted in FIG. 7. It can be seen that features of the 4-MP Raman signal dominate the spectrum of the 4-MP/BPE-SACNs obtained using 785 nm excitation while features of both BPE and 4-MP Raman signals are evident in the spectrum obtained using 633 nm excitation. Thus, by careful choice of two or more different species of Raman-active molecules, and their relative ratios, it is possible to prepare SACNs that provide different Raman scattering spectra depending on the excitation wavelength. This allows an additional level of multiplexing capability.

Example 4

Preparation of Thiol-Active SACNs

A. Silica Modification:
The silica shell of the SACNs can be functionalized to bear free sulfhydryl groups either during the course of making the SiO$_2$ shell ("direct modification"), or after the shell has been completely formed ("post-modification").

B. Post-Modification:
Prepare a 50 mL batch of SACNs according to standard protocols. Proceed through all stages of silica growth, except that the SACNs should be resuspended to only 10 mL in water after the final centrifugation. Assuming negligible losses, this leaves the SACNs at a 5× concentration from the original colloid. Add 40 mL of ethanol to the SACNs. Under moderate magnetic stirring, add 1 mL concentrated NH$_4$OH (30%, J. T. Baker #9733-01). While this is stirring, make a solution that is 900 µL ethanol, 95 µL tetraethylorthosilicate (TEOS, Sigma #333859) and 5 µL (3-mercaptopropyl)trimethoxysilane (MPTMS, Fluka #63800). Add 100 µL of this mixture (effectively 9.5 µL TEOS and 0.5 µL MPTMS) to the stirring SACNs, and allow the reaction to proceed overnight. Purify by repeated centrifugation. Spin down and resuspend the pellet in water a minimum of 3 times to ensure complete removal of ethanol and excess reagents. Resuspend to 5 mL (10×) after the final spin.

C. Direct Modification:
Again, begin to prepare a 50 mL batch of SACNs using typical conditions. The only change is during the Stöber growth step. As before, add 1 mL of concentrated NH$_4$OH and stir for 5 minutes. Then, mix 47.5 µL of TEOS with 2.5 µL of MPTMS, and add them to the tags. Stir overnight and purify by centrifugation, resuspending the purified tags to 5 mL (10×).

Example 5

Bioconjugation of SACNs

With thiol-activated SACNs, biomolecules are attached using the heterobifunctional cross-linker sulfosuccinimidyl 4-[N-maleimidomethyl]cyclohexane-1-carboxylate (sulfo-SMCC, Pierce Biotechnology, Inc). This molecule contains both a maleimide group that is reactive toward sulfhydryls and a sulfo-NHS ester that preferentially reacts with primary amines. In this case, a simple one-pot reaction can used to attach streptavidin, and should be readily adaptable to attachment of most proteins or other molecules that bear primary amines.

Tags may be concentrated prior to conjugation. To conjugate to thiol-activated tags as described above, first add 0.25 mg of streptavidin to 5 mL of 2 mM PBS buffer (0.54 mM KCl, 27.6 mM NaCl, pH=7.4). Add the thiol-activated tags (5 mL at 10× concentration) and mix well. Next, weigh out 1 mg of sulfo-SMCC and add it to the tags and SAv. Immediately mix by vortexing, and react for 1 hour while rotating at room temperature. After 1 hour tags are purified by centrifugation, and resuspension in 2 mM PBS buffer. A small amount (0.1% final concentration) of BSA may be added to minimize the sticking of particles to the centrifuge walls. While this reaction utilizes streptavidin, other proteins (including antibodies) have been conjugated using similar methods. If more control over the reaction is necessary, the protein can be "pre-activated" to adding it to the tags. Because the maleimide group of sulfo-SMCC is quite stable in aqueous solutions (~60 hours), biomolecules can be activated by reaction with sulfo-SMCC for 30-120 minutes followed by purification on a desalting column. This essentially creates a maleimide-activated biomolecule that can be directly added to sulfhydryl-bearing SACBs.

For avidin, analogues (including streptavidin and NeutrAvidin™), and the fluorescent biocytin Alexa Fluor® 594 (Molecular Probes # A12922; "biocytin-594") can be used to quantitate the number of biomolecules bound to the SACNs. The strong visible absorption of the SACNs suggests use of this highly sensitive fluorescent detection rather than using common colorimetric methods (including biotinylated horseradish peroxidase) for streptavidin quantitation. This red-excited dye is useful in a region where the colloidal particles have little absorption which might interfere with measurements. All fluorescence measurements were made using a Fluorolog-3 from Jobin Yvon-Spex.

To alleviate concerns that the highly absorbing SACNs may influence fluorescence measurements, the experiment has been carried out in two different forms. The first is the most straightforward; biofunctionalized particles were incubated in with the biocytin-594 for a given amount of time (nominally 2 hours, protected from light to avoid photobleaching). Tags are then purified by repeated centrifugation (2 times is sufficient if the amount of dye is carefully controlled), and their fluorescence is measured.

The converse to taking direct fluorescence measurements from the tags is to measure the amount of fluorescent molecules that do not bind to the tags. Again, tags are incubated in a carefully chosen amount of dye, and centrifuged just one time. The supernatant is carefully collected and measured for fluorescence. The amount of dye that has bound to the particles can then be determined by subtraction of this value from the known original concentration of dye. One important item to note is that non-stick microcentrifuge tubes (Corning Costar) were used, as the biocytin Alexa Fluor® 594 adsorbs rapidly to the walls of regular tubes. Similar protocols can be used with fluorescently-labeled secondary antibodies if the particles are conjugated to antibodies instead of avidin analogues.

Figure 8:
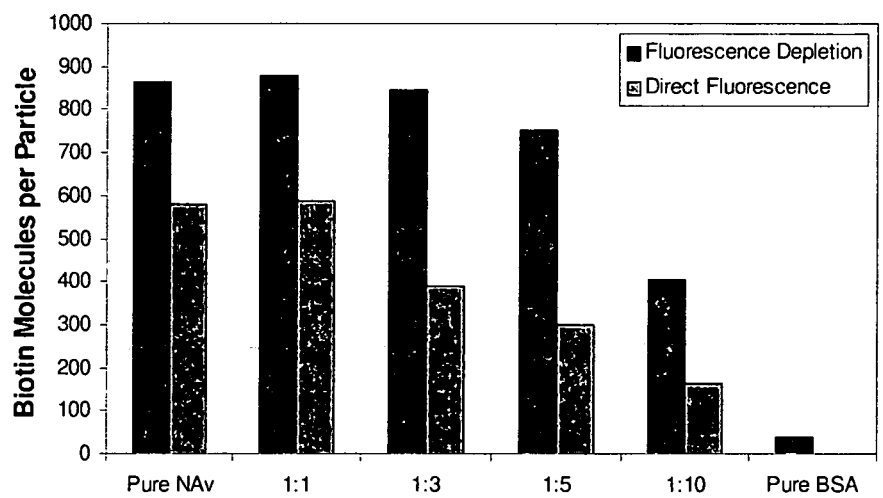
FIG. 8 shows the number of biotin molecules bound to nanoparticles conjugated with varying ratios of NeutrAvidin™ and bovine serum albumin (BSA).

These quantitation methods have been used to show that the amount of a given biomolecule conjugated to the tags can be controlled by adding in another reactive molecule. In FIG. 8, the number of biotin molecules that were bound to nanoparticles conjugated with varying ratios of NeutrAvidin™ and bovine serum albumin (BSA) is shown. Conjugation conditions were equivalent for all reactions, with the ratio of biomolecules being the only variable.

As expected, higher amounts of BSA lead to lower levels of bound biotin. Assuming that each NeutrAvidin™ (NAv) is capable of binding 2 biotins (conjugation to the particle is likely to block some amount of the 4 binding sites), there are up to 300-400 NeutrAvidin™ molecules bound to each tag. But, measurement of the pure BSA-conjugated particles the calculations show less than 10 biocytin-594 molecules bound on each nanoparticle. This is consistent with very low levels of non-specific binding that would be expected by conjugation of BSA (a common blocking reagent) to the particles.

Example 6

Non-Specific Binding Characteristics

As a first characterization step a simple experiment was devised to determine if the streptavidin-coated SACNs could specifically bind biotinylated-BSA. Eight wells of a polystyrene microwell plate were coated with either biotinylated-BSA or BSA by incubating with a 0.5% solution in PBS for thirty minutes. All wells were then washed 4 times with PBS for 1 minute, and then blocked for 30 minutes with a PBS buffer containing 1 mM EDTA, 0.1% BSA and 0.01% Zwittergent 3-08. After aspirating the blocking solution from each well, 20 µL of sample and 20 µL of PBS were added and incubated for 2 hours. The samples comprised neutravidin (NAv)-coated SACNs, streptavidin (SAv)-coated SACNs, SACNs that had been thiol modified (but not conjugated) and control tags with no functionalization of the silica coating. Wells were washed with blocking buffer for 15 minutes, followed by PBS (3×5 min) and water (3×1 min). They were allowed to dry, and the amount of bound tag was quantified by measuring the absorbance at 490 nm using a microwell plate reader (data not shown). Values were background subtracted based on the average absorbance of wells that had not been treated. The NAv and SAv tags bound with high specificity to the biotin coated wells and exhibited little non-specific binding to BSA-coated wells. However, the thiol-coated tags and standard silica-coated tags showed low levels of binding to all wells. Subsequent experiments have shown that this phenomenon can be avoided by blocking the particles by adding a small amount of BSA to the particles, centrifuging and resuspending in PBS. After determining that the SAv- and NAv-conjugated tags were specific for biotin, the number of biotin binding sites that were present on each tag was measured by two methods. A fluorescent biotin analogue, biocytin Alexa Fluor® 594, was reacted with the SACNs. After appropriate wash steps, the number of bound fluorophores was determined by direct measurement and by fluorescence depletion. The values obtained by the two methods were consistent (FIG. 12), although direct fluorescence measurements always produced a lower number. The average number of bound biotins was approximately 700 per nanoparticle under optimal reaction conditions.

Example 7

Oligonucleotide Conjugation

The same sulfo-SMCC chemistry described above was used to bind amine-terminated oligonucleotides to thiol-modified SACNs. After attachment and purification, a dye-labeled complementary strand was incubated with the modified particles. Quantitation of the fluorescent probe (after centrifugation to remove unbound probe) indicated that about 15 oligonucleotides were bound to each nanoparticle. Oligonucleotides were directly attached to NAv-tags, in which the oligonucleotides had a biotin group at one end for attachment to the tag and a fluorophore at the other, to allow a direct measurement of conjugation efficiency. This also yielded approximately 15 oligonucleotides conjugated per nanoparticle. Amine-modified SACNs were coupled to thiol-terminated fluorescent oligonucleotides using the same sulfo-SMCC chemistry described above, again with similar results.

Example 8

Figure 9:
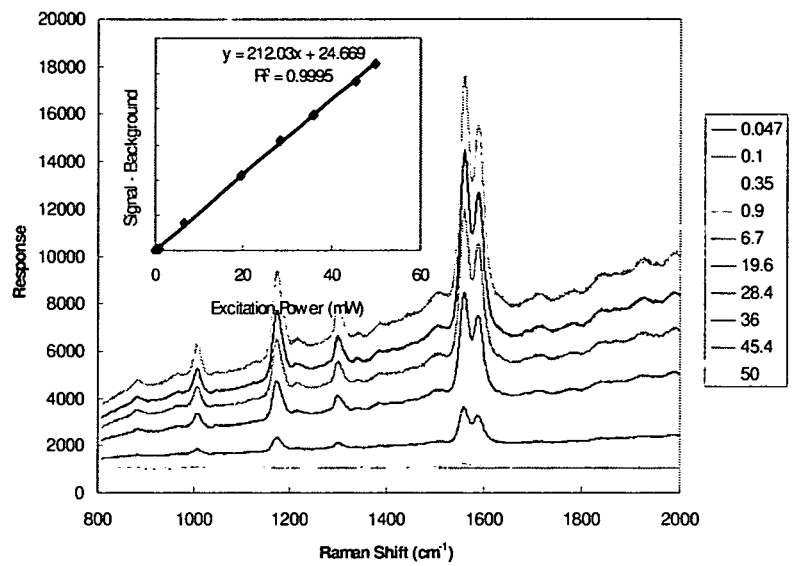
FIG. 9 shows linearity of SACNs by measuring signal after exposing a sample to various amounts of excitation power.

Two characteristics that are desired of quantitative optical tags are that they respond linearly to the excitation source and that they are relatively unaffected by long-term exposure to excitation. The first quality has been demonstrated with SACNs by exposing a sample to various amounts of excitation power and measuring the resulting signal. These results are shown in FIG. 9.

Figure 10:
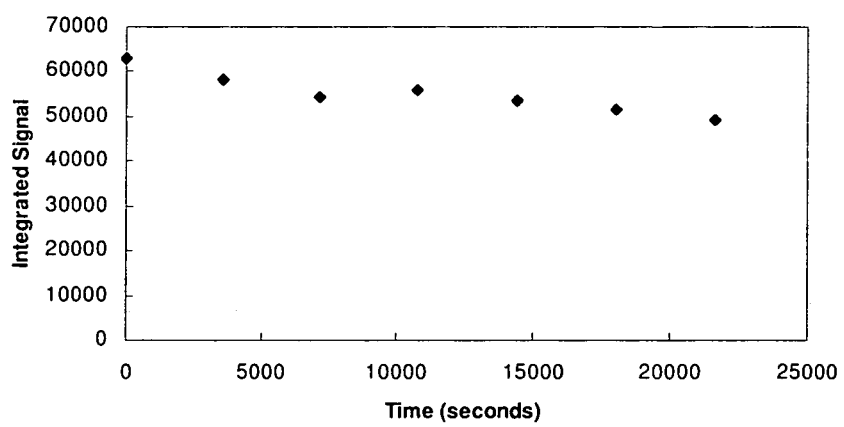
FIG. 10 shows signal from a sample vs. function of time for a SACN exposed to emitted light.

To demonstrate photostability a sample of SACN was deposited on a quartz slide and placed in the sample holder of a Raman spectrometer. For this experiment the spectrometer delivered 60 mW of power at 647.1 nm. The emitted light was collected through a 50×0.8 NA microscope objective, passed through a holographic notch filter to reject Rayleigh scattering, focused into a 0.5 m monochromator and detected with a liquid nitrogen cooled CCD. Spectra were collected approximately every hour for 6 hours during which time the sample was continuously illuminated. The signal from the sample is plotted as a function of time in FIG. 10. This data shows that these particles are quite stable, with only a 20% loss in signal over 6 hours.

Thermal stability of the SACNs is also desirable. To demonstrate this, two batches of 1.5× BPE SACNs (in 35 mL) were boiled for one hour. (The tags were concentrated from 50 mL down to 35 mL, to approx 1.5× concentration. UV-Vis and SERS spectra were recorded before and after boiling. The small differences in absorbance and SERS before and after boiling are mostly attributable to slight difference in concentration. The SACNs are essentially not affected by boiling.

Example 9

Evidence of Batch to Batch Reproducibility

Figure 11:
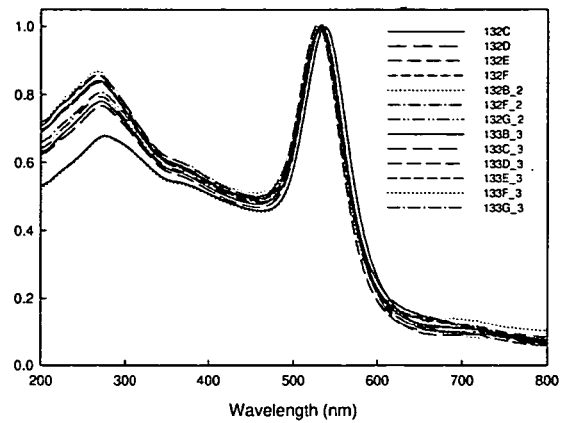
FIG. 11 shows evidence of batch to batch reproducibility for SACN preparation.

To determine the reproducibility of making tags from start to finish of the process, a total of 6 colloids were made and were labeled B-G. These colloids were used to prepare a total of 13 different batches of tags, using identical protocols for each batch. The (normalized) absorption spectra of these colloids are shown in FIG. 11, and it is apparent that they are quite similar after all steps are complete.

After normalizing the concentration by equilibrating the optical density of each solution to 1.0, the SERS response was measured using 785 nm excitation. SERS signals were monitored at the major peak (~1200 cm$^{-1}$) (not shown). Using all samples, the RSD of the group is 12.5%. If one significant outlier is removed, the remaining twelve samples exhibit an RSD of 7.5%.

Example 10

A. Preparation of Anisotropic Nanorods with Diameter 18-90 nm

Commercially available templates with different pore size (18 nm to 90 nm) were used for electrodeposition of anisotropic Au nanorods. Evaporated Ag, about 1 µm thick, served as a plating substrate. Immediately before electrodeposition the template was assembled into the electrochemical cell and soaked in Ag-plating solution under house vacuum for 1 hr for ensuring proper wetting of the pores, followed by electrodeposition into the pores of 1 µm thick fresh Ag. Subsequently the electrodeposition of nanowires consisting of alternating Au and Ag stripes occurred. Commercial plating solutions were used: Cyless Silver (Technic, Inc.) and Microfab Au 100 (Sulfite-based Au-solution from Enthone-OMI, Inc.). The length of the Au segments was determined by the desired aspect ratio of the Au nanorods; the length of the Ag segments could be in the range of 10-200 nm; the total number of stripes per pore was determined by the desired final (after release from template) concentration of Au nanorods/ml solution.

Different plating techniques were used depending on template pore diameter. For pore diameter of 65 nm and 90 nm, a semi-automated synthesizer for Nanobarcodes particles was used in constant current mode. Plating of AuAg-nanowires with 59 stripes (each stripe 30 nm long) sequentially plated into one template leading after Ag-removal to 3×10$^{11}$ Au nanorods/template has been demonstrated.

Figures 12A, 12B:
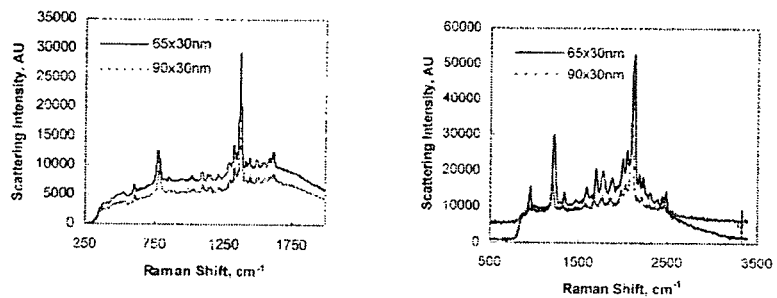
FIG. 12A shows Raman spectra obtained at 633 nm excitation of 65×30 nm and 90×30 nm Au particles released in QSH.
FIG. 12B shows Raman spectra obtained at 785 nm excitation of 65×30 nm and 90×30 nm Au particles released in QSH.
Figure 13:
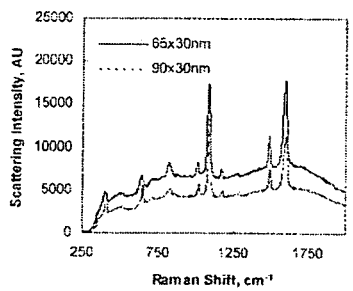
FIG. 13 shows Raman spectra obtained at 633 nm excitation of 65×30 nm and 90×30 nm Au particles released in MP.

A release protocol was developed starting with the dissolution of the Ag (substrate and Ag-stripes) in Nitric acid, followed by template dissolution in NaOH. To prevent dumpiness of the released Au nanorods a short SAM-molecule (self-assembled monolayer) was added to the NaOH during template dissolution. Examples for short thiol-containing molecules are mercaptoethanol (ME), mercaptopropionic acid (MPA) and mercaptoethanesulfonic acid (MESA). These short molecules were later replaced with the Raman reporter molecule. An alternative method which produced better results was to introduce the Raman reporter molecule directly to the NaOH during template dissolution. 4-Mercaptophenol (MP) and 2-quinolinethiol (QSH) were successfully used and demonstrated Raman signal with Au nanorods. FIG. 12 shows the Raman spectra of 65×30 nm and 90×30 nm Au particles released in QSH. FIG. 13 illustrates the Raman spectra of 65×30 nm and 90×30 nm Au particles released in MP.

The constant current mode of electrodeposition was not efficacious for templates with pore diameter of 35 nm and less. Different pulse plating techniques (pulse current, reverse pulse current and double pulse) may be used. Using polycarbonate templates with hole diameter in the submicron range, reverse current electrodeposition with ultrasonic agitation has been applied successfully to grow Au single-crystals from cyanide solutions. However, polycrystalline Au was deposited from Au-sulfite solutions using a variety of reverse pulse conditions: Dobrev, D; Vetter, J.; Angert, N.; Neumann, R.; Electrochimica Acta 2000, 45, 3117-3125. It has been shown earlier that pulsed potentiostatic deposition from Au-sulfite solution improved the metal distribution onto photoresist patterned structures but didn't strongly influence the properties (stress, purity, resistance) of the Au-films, which was explained by the irreversibility of Au/Au(I) couple in sulfite solutions: Horkans, J.; Romankiw, L. T.; J. Electrochem. Soc. 1977, 124, 1499-1505.

The pulse parameters (pulse current, frequency and duty cycle) have been varied in such manner that the average plating current was somewhat low (0.25-1 mA/sqcm) to ensure a slow growth of the Au and Ag stripes. Successful plating was achieved at the following pulse plating conditions: pulse current of 2 mA/sqcm; frequency range 0.025-2.5 Hz and duty cycle 0.1-0.3. The same pulse conditions were used for both Au and Ag-stripes within one experiment. A Multichannel Potentiostat/Galvanostat (Princeton Applied Research) was used; after plating of each stripe the solution was changed followed by rinse and refill with the next solution manually. Plating of 19 alternating Au/Ag stripes yielding, after Ag-removal, 3×E11 Au nanorods/template (35 nm pore diameter) and 1×E12 Au nanorods/template (18 nm pore diameter) has been demonstrated. Automation of the pulse plating may further increase the number of particles by another order of magnitude because the template thickness is 50 μm. FIG. 14 shows a TEM image of Au nanorods with 35 nm diameter, released in ME and the Raman spectrum of the nanorods after replacement of ME with QSH.

B. Preparation of Anisotropic Au Particles of 250 nm×250 nm 250 nm×250 nm Au particles were prepared similar to the particles in part A. Alumina templates with pore size 250 nm were used for electrodeposition of Au nanoparticles. Evaporated Ag, about 1 μm thick, served as a plating substrate. Fresh Ag, 5 μm thick, was electrodeposited into the holes for additional sealing of the template, followed by sequential electrodeposition of nanowires consisting of alternating Au and Ag stripes, each 250 nm long. Commercial plating solutions were used: Cyless Silver (Technic, Inc.) and Microfab Au 100 (Enthone-OMI, Inc.). A semi-automated synthesizer for Nanobarcodes particles was used for plating of 9 Au and Ag-stripes, each at a const current of 1 mA. A release protocol was developed starting with the dissolution of the Ag (substrate and Ag-stripes) in Nitric acid, followed by template dissolution in Sodium Hydroxide. To prevent clumpiness of the released Au nanoparticles a thiol-Raman reporter molecule, 4-Mercaptophenol (MP), pre-dissolved in Ethanol (EtOH) was introduced to the Sodium Hydroxide during release. The release steps were as follows:
1. 12 ml 40% $HNO_3$, 60 min
2. 2 ml 28 mM MP/EtOH+8 ml 3M NaOH/20% EtOH/80% $H_2O$, 30 min
3. 200 μl 28 mM MP/EtOH+800 μl 3M NaOH/20% EtOH/80% $H_2O$, 30 min
4. Centrifuge: 4200 rpm, 2 min
5. 3× rinse 200 μl MP/EtOH+800 μl EtOH/$H_2O$ (1:4)
6. Centrifuge: 4200 rpm, 1 min after each SEM/TEM sample, 10 μl each
7. 0.1 ml sample: dilute to 1 ml with $H_2O$ for UV-vis
8. 2× rinse $H_2O$, centrifuge at 6200 rpm, 10 min each
9. Acquire Raman.

The concentration of Au-particles after the release was $5\times10^9$/ml. The gold particles were re-suspended in Ethanol and a 300 μL aliquot was taken for glass coating. 490 μL Ethanol, 160 μL 18 M water, 10 μL 30% Ammonium Hydroxide, and 40 μL neat Tetraethylorthosilicate (TEOS) were added to the aliquot of gold particles. The sample was sonicated and placed on a vortexer at the lowest setting to mix for 45 minutes. The sample was then rinsed three times in 18 M water. FIGS. 15A and B show SEM images for the resulting anisotropic particles. FIGS. 16A and B show a closer view of a single particle. Raman spectra of the particles are shown in FIGS. 17A and B.

Example 11

IL7 Sandwich Immunoassay

Figure 18:
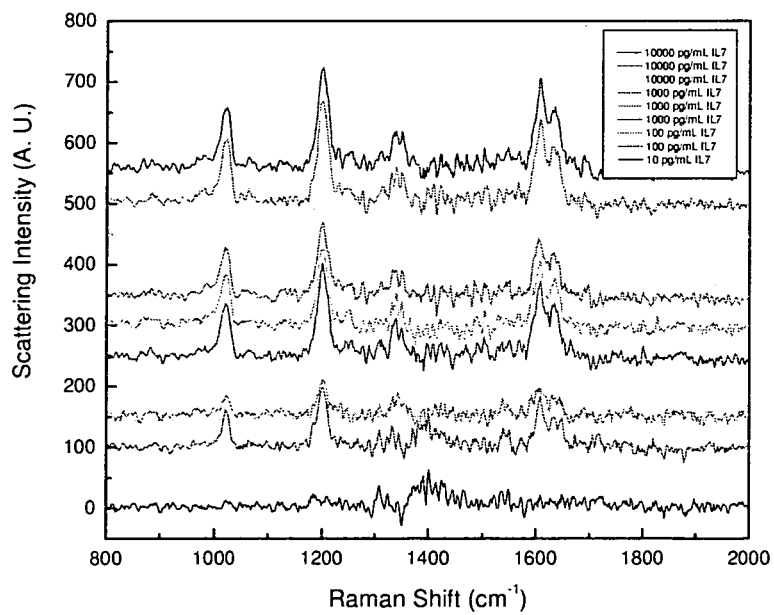
FIG. 18 shows the results of a protein microarray sandwich immunoassay experiment in which IL-7 was titrated.

A protein microarray experiment was simulated by printing capture IL-7 antibodies onto a microarray slide. Each spot was approximately 500 μm on a side, and repeated six times on each glass substrate (printed by Telechem, Inc., Sunnyvale, Calif.). A hydrophobic pen was used to provide a liquid barrier on the glass slide so each of the six spots may be treated independently. After the pen dried, the slide was blocked for at least 60 minutes with 5% bovine serum albumin (BSA) in 10 mM phosphate buffered saline (PBS). All incubation and wash steps were carried out on an orbital rocker or shaker, and solutions were aspirated by pipette prior to addition of new solutions. After blocking, slides were washed 3 times for 5 minutes each (3×5) with 0.5% BSA/PBS. Antigens were prepared in a 0.5% BSA/PBS solution and incubated on the arrays for 45 minutes to 2 hours, after which arrays were once again washed (3×5) in 0.5% BSA/PBS. IL7-modified SACNs (using biotinylated antibodies onto neutravidin coated SACNs) were then incubated on the arrays for 90 minutes. This was followed by a wash (3×5) in 0.5% BSA/PBS and quick rinses in PBS and water. Slides were blown dry by a jet of nitrogen gas immediately after the water rinse. Raman spectra from these arrays were acquired using a diode laser (785 nm, 200 mW) and an Ocean Optics USB-2000 spectrometer and software. The typical integration time for spectra acquired on glass arrays was two seconds. Background subtraction was used to remove the broad glass background from all spectra. Without optimization a limit of detection between 10-100 pg/ml (FIG. 18) was achieved, which is comparable to many commercial enzyme immunoassays. The potential for multiplex assays was then demonstrated, by probing three different analytes (ovalbumin, bacillus globigii, and C-reactive protein) on adjacent spots of a protein chip. Antibodies to each antigen were conjugated to SACNs with different reporter molecules giving BPE-anti Bg, QSH-anti Ova, and Bodipy-anti CRP particles. An array of spots containing capture antibodies to the antigens was exposed to a mixture of all three antigens. After appropriate rinsing the spots were exposed to all three detection SACNs. Raman spectra were then collected from each of the spots. The data show a clean signal at each spot, with the spot that was designed to capture CRP giving a strong Bodipy tag signal, for example.

Example 12

Figure 19:
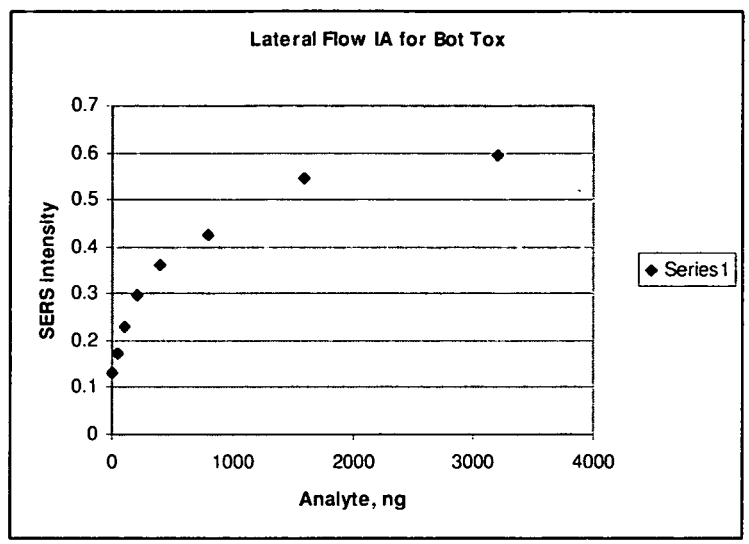
FIG. 19 shows the results of a lateral flow immunoassay for Bot tox.

A lateral flow immunoassay for Bot tox was undertaken, using Tetracore, Inc.'s (Gaithersburg, Md.) lateral flow cartridge. In this experiment, the device was opened, removed the pad containing their calorimetric detection reagent (which comprises colloidal Au conjugated to a detection Ab), and replaced it with a conjugate comprising SACNs conjugated to the same Ab (provided by Tetracore). Raman spectra were collected using the instrument previously described. The data show minimal non-specific binding, and successful capture of the conjugate in the presence of antigen, with a non-optimized limit of detection similar to their commercial product. Results are shown in FIG. 19.

Example 13

Staining of SK-BR3 Cells with SACNs

Figure 21A:
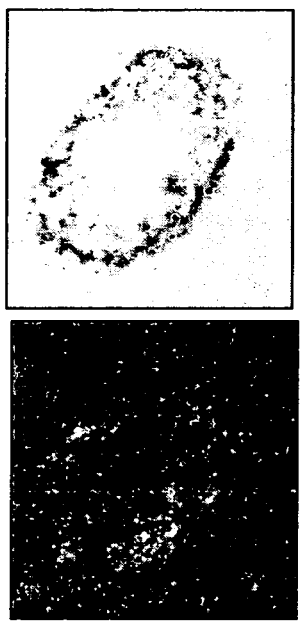
FIG. 21A shows bright field and SERS images of SACN-labeled, cell.

Cells were cultured on a chamber slide. Cells were washed with PBS three times, 1 min each. Cells were fixed with 3.7% formaldehyde/PBS for 10 min at room temperature, and washed as before. Cells were blocked with 1% BSA/PBS for 20 min at room temperature. Cells were incubated with 1 µg/ml mouse anti-her2 antibodies (diluted with block buffer) for 30 min at room temperature, then washed as above. Cells were then incubated with 1 µg/ml biotinylated anti-mouse IgG for 30 min, and washed as before. The cells were incubated with 50 µl of 2× streptavidin conjugated SACN at room temperature for 1 hr, and washed as before. Hoechest dye (diluted 1:500) was added and the cells incubated for 5 minutes. The cells were washed as before. The cells were mounted with a coverslip using 90% glycerol in PBS, and the edges were sealed with nail polish. FIG. 21A shows bright field and SERS images of the resulting sample, and demonstrate binding of SACNs to specific locations on the cell surface and the cell interior.

Example 14

Detection of SACNs in Tissue Samples

Figure 21B:
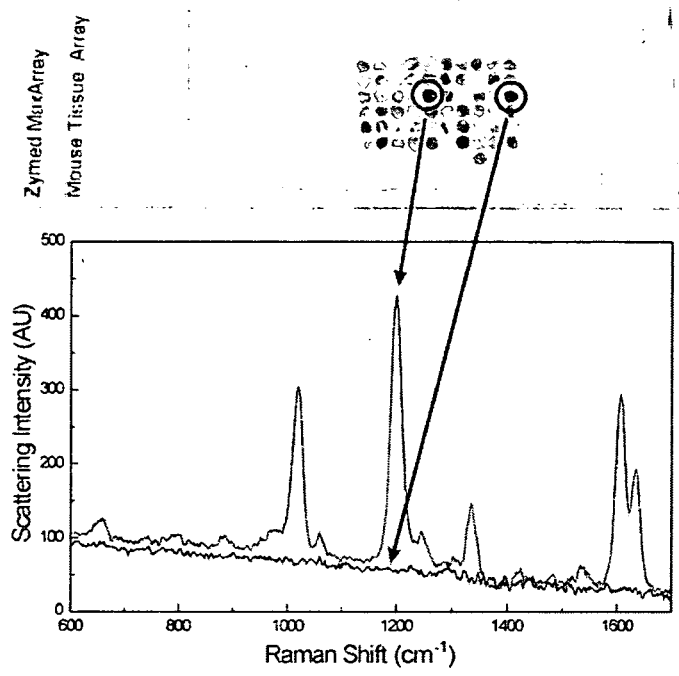
FIG. 21B shows and Raman spectra from untreated and treated spots in a histopathology assay.

SACNs particles can also be detected in the presence of tissue samples stained with strongly colored organic dyes. For example, hematoxylin and eosin (H&E) are the standard dyes used to visualize cell size and shape. Both molecules exhibit fluorescence in the visible, making use of conventional immunohistochemical methods on the same sample difficult or impossible. However, with 785 nm excitation, a minimal background is obtained, rendering the SACNs easily visualizable. Thus, a mouse tissue array from Zymed was treated with H&E according to standard histopathology protocols, resulting in highly colored spots. Several spots were treated with polylysine and then BPE SACNs. FIG. 21B shows Raman spectra from untreated and treated spots, indicating the ease with which SACNs can be seen over a background of H&E stains. Accordingly, the present invention provides 1. A method, comprising contacting a tissue sample with at least one biomolecule-conjugated SACN particle capable of specifically binding to the tissue sample; and acquiring a Raman image of the tissue/biomolecule-conjugated SACN particles mixture. The tissue is contacted with one or more additional non-SACN reagents, such as eosin, hemotoxylin, and a combination of hemotoxylin and eosin. Background Raman image of a tissue sample may be obtained and subtracted from the Raman image of the tissue/biomolecule-conjugated SACN particles mixture. Additionally, the Raman image may further be compared with the Raman image with an image of a tissue sample which has been stained with strongly colored organic dyes to visualize cell size and shape, such as an H&E stain.

Example 15

In vivo Labeling of Animals with SACNs

SACNs were injected into nude mice in 2 ways: a) by tail injection for circulation in the blood stream; and b) by subcutaneous injection for localization under the skin. In both cases the optical probe was held over the skin and the Raman signal detected emitted from below the skin. The peaks of the SACNs could be seen above the background. The portable detection system had a 785 nm laser for excitation manufactured by Ahura Corp. 106 mW of light was delivered to the specimen via an optical fiber and optical head manufacture by InPhotonics Inc. Raman scattered light was detected by the same optical head. A dichroic filter sends the collected light to a second optical fiber, attached to a spectrometer, Ocean Optics USB2000, with a 50-micron slit and 1200 grooves/mm grating blazed at 750 nm. The spectrometer data was collected by a laptop computer.

Figure 22:
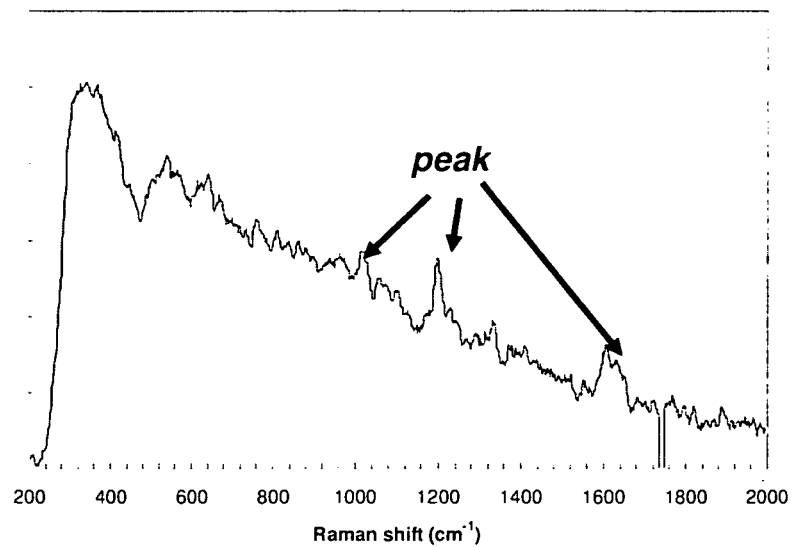
FIG. 22 shows a spectrum acquired over the liver 45 minutes after SACNs were injected into the mouse tail.

In the case of a) signal was detected at approximately 45 minutes. At this time a signal was detected when the probe was held over the mouse liver, FIG. 22. The SERS tag spectrum appears on a background that is a mixture of tissue fluorescence and Rayleigh back scatter. The actual background measured depends on the probe position over the skin. If the probe is in contact with the skin, then the spectra may contain more tissue fluorescence. If the probe is offset from the skin, the spectra may contain more Rayleigh backscatter. For example, in the case of a spectrum acquired at the liver, and a spectrum acquired at the flank of the mouse, the backgrounds are different. Since the background can vary, SACNs have an advantage since the tags can be quantified by the peak height over background.

Figure 23:
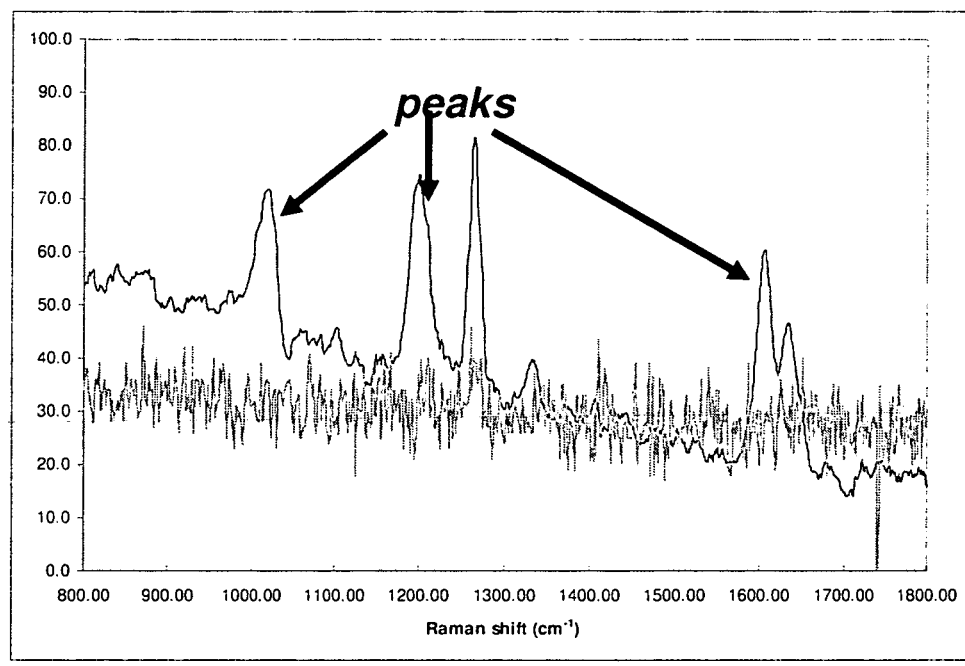
FIG. 23 shows a spectrum acquired after SACNs were injected subcutaneously.

In the case of b) the signal was detected immediately after injection, as shown in FIG. 23. FIG. 23 also contains a spectrum taken from a mouse with no SACN, acquired at the flank. The signal would diminish over time as the tag diffused into the body of the mouse. The subcutaneous spectrum also contains some background fluorescence and Rayleigh scatter, however the SACN signal is much stronger over the background.

Example 16

Multiplexed Cellular Imaging Experiments

The cell line LNCaP, an androgen-sensitive, adherent cell line derived from a human prostate carcinoma, will be used. LNCaP cells are available from ATCC (Rockville, Md.). LNCaP cells are excellent models for prostate cancer. There are a number of commercially available antibodies to biomarkers that are known to be important in prostate cancer, such as alpha-methylacyl-CoA racemase (AMACR) and Prostate Specific Antigen (PSA). Other antibodies useful as markers or controls include antibodies to CDH1, CTNNB1, CCND1, HPN, TP53, CDKN1B, and BCL2.

Antibodies to these markers will be conjugated to SACNs. Cellular labeling and imaging experiments in which LNCaP cells are treated with various compounds and conditions will be performed. The effect on the cell viability, and the spatial localization of the antibody conjugated SACNs will be monitored.

SACNs conjugated to both AMACR antibodies and PSA antibodies will be used to compare protein expression of AMACR and PSA in the cell lines LNCaP, DU-145 and PC-3 as detailed by Kuefer, et al., *Am J Pathol* 2002, 161, 841-48. Cells will be treated with bicalutamide, an oral medication from the anti-androgen class of prescription drug treatments for prostate cancer. LNCaP, a hormone-sensitive tumor cell line, demonstrates stronger AMACR expression by Western blot analysis than do cell lines DU-145 and PC-3. Upon treating the LNCaP cells with bicalutamide, the AMACR protein expression in cells remains unchanged, whereas prostate-specific antigen, known to be androgen-regulated, demonstrates decreased protein expression. Spatial localization of the SACNs will be performed. In intracellular imaging, unlike surface labeling experiments, it is not possible to wash away unbound tags. These experiments will therefore allow us to understand what happens to excess SACNs that are not bound to a specific target within the cell (for example, if that target is down-regulated, such as PSA in this assay).

Arnold, et al., *Am. J. Physiol. Endocrinol Metab.* 2004, 288, E573-E584 recently published a study of the effect of dehydroepiandrosterone (DHEA), an over-the-counter dietary supplement, on the gene and protein expression of LNCaP cells. They found that DHEA affected cell proliferation and increased the protein expression of PSA as well as a number of IGF receptors. Using SACNs conjugated to PSA antibodies, and antibodies indicative of cell growth in cancer cells, such as CCND1 (cyclin D1), this biological system will be investigated. The cells will be treated with DHEA, testosterone, retinoic acid, and 17beta-estradiol (E2), and compare the cellular imaging results with those reported by Arnold et al.

What is claimed is:

1. A Surface Enhanced Spectroscopy-Active Composite Nanoparticle (SACH), comprising a nanoparticle core, a Raman-active reporter molecule associated with the nanoparticle core, and an $SiO_2$ encapsulant which encapsulates the nanoparticle core and the reporter molecule; wherein the encapsulant comprises a reactive group chosen from —SH, —$NH_2$, or —$COO^-$.

2. The SACN of claim 1, wherein the nanoparticle core has a spheroid, rod, disk, pyramid, cube, cylinder, nanohelix, nanospring, nanoring, arrow, teardrop, tetrapod, or prism shape.

3. The SACN of claim 2, wherein the nanoparticle core is rod-shaped, and has a diameter of about 250 nm and a length of about 250 nm.

4. The SACN of claim 1, wherein the nanoparticle core has internal surface area.

5. The SACN of claim 4, wherein the nanoparticle core is porous.

6. The SACN of claim 1, wherein the Raman-active reporter molecule comprises pyridine, triazine, pyrimidine, pyrrole, oxazole, imidazole, furan, cyanide, cyanamide, or acetylene, or a derivative thereof; or comprises a molecule having at least one reactive croup chosen from nitro, nitroso, —$CCl_2$, —$CCl_3$, isothiocyanate, or isocyanide.

7. The SACN of claim 1, wherein the Raman-active reporter molecule comprises a molecule having a reactive group chosen from cyanide, $SCN^-$, $ClO_3^-$, or $HCO_2^-$.

8. The SACN of claim 1, wherein the Raman-active reporter molecule comprises a transition metal.

9. A Surface Enhanced Spectroscopy-Active Composite Nanoparticle (SACN) comprising:
 a) a core/shell nanoparticle comprising a nanoparticle core covered with a shell, wherein the core and the shell may comprise the same or different materials;
 b) at least one Raman-active reporter molecule associated with said core/shell nanoparticle; and
 c) an $SiO_2$ encapsulant which encapsulates the core/shell nanoparticle and the at least one Raman-active reporter molecule.

10. The SACN of claim 9, wherein said core/shell nanoparticle comprises an $Au_2S$ core/Au shell nanoparticle, an Ag core/Au shell nanoparticle, a silica core/Au shell nanoparticle, a silica core/Ag shell nanoparticle, an alumina core/Au shell nanoparticle, an alumina core/Ag shell nanoparticle, a $TiO_2$ core/Au shell nanoparticle, or a $TiO_2$ core/Ag shell nanoparticle.

11. A Surface Enhanced Spectroscopy-Active Composite Nanoparticle (SACN) comprising:
 a core/shell nanoparticle comprising a nanoparticle core covered with a shell, wherein the core and the shell may comprise the same or different materials,
 a Raman-active reporter molecule associated with the core/shell nanoparticle, and
 an $SiO_2$ encapsulant which encapsulates the core/shell nanoparticle and the Raman-active reporter molecule, wherein the encapsulant comprises a reactive group chosen from —SH, —$NH_2$, or —$COO^-$.

12. The SACN of claim 11, wherein said core/shell nanoparticle comprises an $Au_2S$ core/Au shell nanoparticle, an Ag core/Au shell nanoparticle, a silica core/Au shell nanoparticle, a silica core/Ag shell nanoparticle, an alumina core/Au shell nanoparticle, an alumina core/Ag shell nanoparticle, a $TiO_2$ core/Au shell nanoparticle, or a $TiO_2$ core/Ag shell nanoparticle.

13. The SACN of claim 11, wherein the Raman-active reporter molecule comprises pyridine, triazine, pyrimidine, pyrrole, oxazole, imidazole, furan, cyanide, cyanamide, or acetylene, or a derivative thereof; or comprises a molecule having at least one reactive group chosen from nitro, nitroso, —$CCl_2$, —$CCl_3$, isothiocyanate, or isocyanide.

14. The SACN of claim 11, wherein the Raman-active reporter molecule comprises a molecule having a functional group chosen from cyanide, $SCN^-$, $ClO_3^-$, or $HCO_2^-$.

15. The SACN of claim 11, wherein the Raman-active reporter molecule comprises a transition metal.

* * * * *